(12) United States Patent
Jones et al.

(10) Patent No.: US 10,627,404 B2
(45) Date of Patent: Apr. 21, 2020

(54) METHODS AND COMPOSITIONS FOR BIOSENSING

(71) Applicant: The University of North Carolina at Charlotte, Charlotte, NC (US)

(72) Inventors: Marcus Jones, Huntersville, NC (US); Kirill Afonin, Charlotte, NC (US)

(*) Notice: Subject to any disclaimer, the term of this patent is extended or adjusted under 35 U.S.C. 154(b) by 0 days.

(21) Appl. No.: 15/630,186

(22) Filed: Jun. 22, 2017

(65) Prior Publication Data

US 2017/0370939 A1 Dec. 28, 2017

Related U.S. Application Data

(60) Provisional application No. 62/353,155, filed on Jun. 22, 2016.

(51) Int. Cl.
| | |
|---|---|
| *C12Q 1/68* | (2018.01) |
| *G01N 33/58* | (2006.01) |
| *C12Q 1/6825* | (2018.01) |
| *G01N 21/64* | (2006.01) |
| *C12Q 1/6804* | (2018.01) |

(52) U.S. Cl.
CPC ......... *G01N 33/588* (2013.01); *C12Q 1/6804* (2013.01); *C12Q 1/6825* (2013.01); *G01N 21/6428* (2013.01); *G01N 2021/6439* (2013.01)

(58) Field of Classification Search
CPC ............ C12Q 1/6804; C12Q 2563/107; C12Q 2563/149; C12Q 1/6825; G01N 33/588
See application file for complete search history.

(56) References Cited

U.S. PATENT DOCUMENTS

| | | | |
|---|---|---|---|
| 8,691,500 B2 | 4/2014 | Kim et al. | |
| 2005/0136258 A1* | 6/2005 | Nie ................... | A61K 49/0017 428/402 |
| 2011/0171789 A1 | 7/2011 | Korgel et al. | |
| 2013/0115713 A1 | 5/2013 | Mountziaris et al. | |
| 2013/0281315 A1* | 10/2013 | Sandros ................ | C12Q 1/682 506/9 |
| 2015/0112612 A1 | 4/2015 | Walt et al. | |

OTHER PUBLICATIONS

Chan et al "Quantum dot bioconjugates for ultrasensitive nonisotopic detection" Science, 1998, 281: 2016-2018. (Year: 1998).*

* cited by examiner

*Primary Examiner* — Betty J Forman
(74) *Attorney, Agent, or Firm* — J. Clinton Wimbish; Nexsen Pruet, PLLC

(57) ABSTRACT

In one aspect, methods of sensing are described herein. In some embodiments, such a method comprises disposing a population of luminescent species in a test sample, exposing the test sample to electromagnetic radiation having a wavelength corresponding to an excitation wavelength of the luminescent species, detecting light emitted by the luminescent species within a detection region of the test sample, and correlating the light emitted by the luminescent species within the detection region to a presence or absence of an analyte within the test sample. The luminescent species, in a non-aggregated state, exhibits luminescence blinking and, in an aggregated state, does not exhibit luminescence blinking. Additionally, correlating the light emitted by the luminescent species to the presence or absence of the analyte comprises determining whether the light emitted by the luminescent species within the detection region is blinking luminescence or non-blinking luminescence.

5 Claims, 8 Drawing Sheets

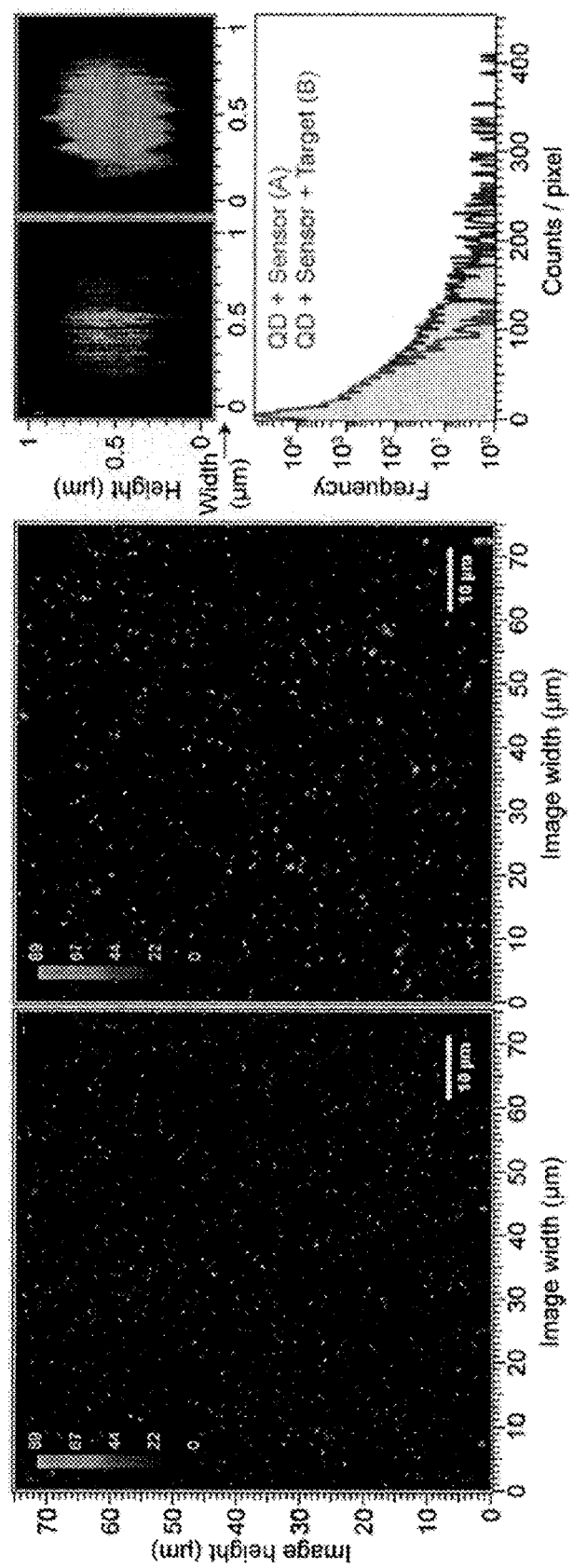

METHODS AND COMPOSITIONS FOR BIOSENSING

CROSS REFERENCE TO RELATED APPLICATIONS

This application claims priority pursuant to 35 U.S.C. § 119(e) to U.S. Provisional Patent Application Ser. No. 62/353,155, filed on Jun. 22, 2016, which is hereby incorporated by reference in its entirety.

FIELD

This invention relates to the sensing or detection of biological materials and, in particular, to compositions and methods for biosensing using quantum dots (QDs).

BACKGROUND

Various luminescent species have been used for sensing applications, including biosensing applications. Such luminescent species include so-called "quantum dots" (QDs) or semiconductor nanocrystals. Previous QD-based biosensing methods rely on changes in QD fluorescence intensity or color caused by interactions between an analyte and a QD. For such sensing to occur, QDs must be engineered with a local coordination environment that, after selective interaction with an analyte, is able to undergo an electron or energy transfer reaction with the QD. Thus, in these approaches, the analyte must induce one or more physical or chemical changes that modify the fluorescence of individual QDs. The signal from this type of sensor is usually straightforward to detect, but it is often difficult or impossible to design a QD-based system that can undergo such dramatic fluorescence changes, which are inherently sensitive to donor-acceptor distances and small changes in the local environment. Additionally, reliance on changes in fluorescence of individual QDs due to analyte-QD interactions makes it difficult to build a general QD-based sensor that can be modified for a wide range of analytes without radically changing the design of the sensor for a given analyte of interest. Therefore, development of new compositions and methods for biosensing is needed, including new sensing compositions and methods relying on QD luminescence.

SUMMARY

Compositions and methods are described herein which, in some embodiments, provide one or more advantages compared to previous compositions and methods, including for the sensing or detection of biological materials or other materials. For example, in some cases, compositions and methods described herein can be readily modified for detecting a desired analyte, without the need to substantially redesign or reconfigure the luminescent species used for reporting the presence or absence of the analyte. Compositions and methods described herein can also provide QD-based sensing without the need to rely on charge transfer or energy transfer between a QD fluorophore and its microenvironment in response to an analyte. Additionally, compositions and methods described herein, in some embodiments, provide lower detection limits of biological molecules due to assembly or disassembly of a plurality of luminescent species in response to a single analyte molecule. Further, QD-based sensing compositions described herein, in some instances, exhibit a long shelf-life.

In one aspect, methods of sensing are described herein. In some embodiments, such a method comprises disposing a population of luminescent species in a test sample, exposing the test sample to electromagnetic radiation having a wavelength corresponding to an excitation wavelength of the luminescent species, and detecting light emitted by the luminescent species within a detection region of the test sample. The method further comprises correlating the light emitted by the luminescent species within the detection region to a presence or absence of an analyte within the test sample in an amount above a minimum detection threshold. Moreover, the luminescent species, in a non-aggregated state, exhibits luminescence blinking and, in an aggregated state, does not exhibit luminescence blinking Additionally, correlating the light emitted by the luminescent species within the detection region to the presence or absence of the analyte within the test sample comprises determining whether the light emitted by the luminescent species within the detection region is blinking luminescence or non-blinking luminescence. Further, in some preferred embodiments, the luminescent species of a method described above comprise colloidal quantum dots (QDs), and the analyte comprises a nucleic acid. However, other luminescent species and analytes may also be used.

Moreover, in some cases, a method described herein is based on an "assembly" approach, in which the presence of the analyte is accompanied by the assembly or aggregation of luminescent species and, concomitantly, the detection of non-blinking luminescence. For example, in some instances, the population of luminescent species, when initially disposed in the test sample, is in the non-aggregated state, and the presence of the analyte within the test sample causes the population of luminescent species to transition from the non-aggregated state to the aggregated state, resulting in detection of non-blinking luminescence.

Further, in some such cases, one or more additional steps can be used to facilitate the assembly of a plurality of individual luminescent species. For instance, in some embodiments, a method described herein further comprises disposing an analyte binding species (or more than one analyte binding species) in the test sample prior to disposing the population of luminescent species in the test sample. The one or more analyte binding species, in the presence of the analyte, binds to the analyte and forms one or more coupling species or coupling agents. In the absence of the analyte, the analyte binding species does not form the coupling species. Moreover, the coupling species, when formed in the presence of the analyte, is operable to couple or aggregate a plurality of the luminescent species to one another. In some instances, the coupling species is operable to couple two of the luminescent species to one another. In other embodiments, the coupling species is operable to couple more than two of the luminescent species to one another. Further, in some cases, individual luminescent species of the population of luminescent species comprise one or more moieties for binding to the coupling species. As described further hereinbelow, it is also possible that the analyte itself, rather than a separate coupling species, couples or attaches luminescent species to one another.

Methods described herein may also be based on a "disassembly" approach rather than an "assembly" approach. In a "disassembly" approach, the presence of the analyte is accompanied by the disassembly, disaggregation, disintegration, or uncoupling of luminescent species and, concomitantly, the detection of blinking luminescence. For example, in some instances, the population of luminescent species, when initially disposed in the test sample, is in the aggregated state, and the presence of the analyte within the test sample causes the population of luminescent species to transition from the aggregated state to the non-aggregated state, resulting in detection of blinking luminescence.

In another aspect, sensing compositions are described herein. As with methods of sensing described above, sensing compositions described herein can be operable to detect an analyte by "assembly" or "disassembly" of individual luminescent species of the composition. For example, in some embodiments, a composition described herein comprises a population of individual luminescent species, wherein the luminescent species, in a non-aggregated state, exhibits luminescence blinking and, in an aggregated state, does not exhibit luminescence blinking. Further, the individual luminescent species are operable to transition from the non-aggregated state to the aggregated state in the presence of an analyte, including in a manner described herein for methods of sensing. Alternatively, in other cases, a sensing composition described herein comprises a coupled or aggregated luminescent species formed from an aggregate of individual luminescent species. The individual luminescent species, in a non-aggregated state, exhibit luminescence blinking and, in an aggregated state, do not exhibit luminescence blinking. Moreover, the coupled luminescent species is operable to transition from the aggregated state to the non-aggregated state in the presence of an analyte, including in a manner described herein for methods of sensing. Additionally, in some preferred embodiments of sensing compositions described herein, the individual luminescent species comprise colloidal quantum dots.

These and other embodiments are described in greater detail in the detailed description which follows.

BRIEF DESCRIPTION OF THE DRAWINGS

FIGS. 3A and 3B are each fluorescence microscopy images of luminescent species of sensing compositions and methods according to some embodiments described herein.

FIGS. 3C and 3D are reimaged portions of FIGS. 3A and 3B, respectively.

FIG. 3E illustrates intensity histogram data for the compositions of FIGS. 3A and 3B.

DETAILED DESCRIPTION

Figure 1:
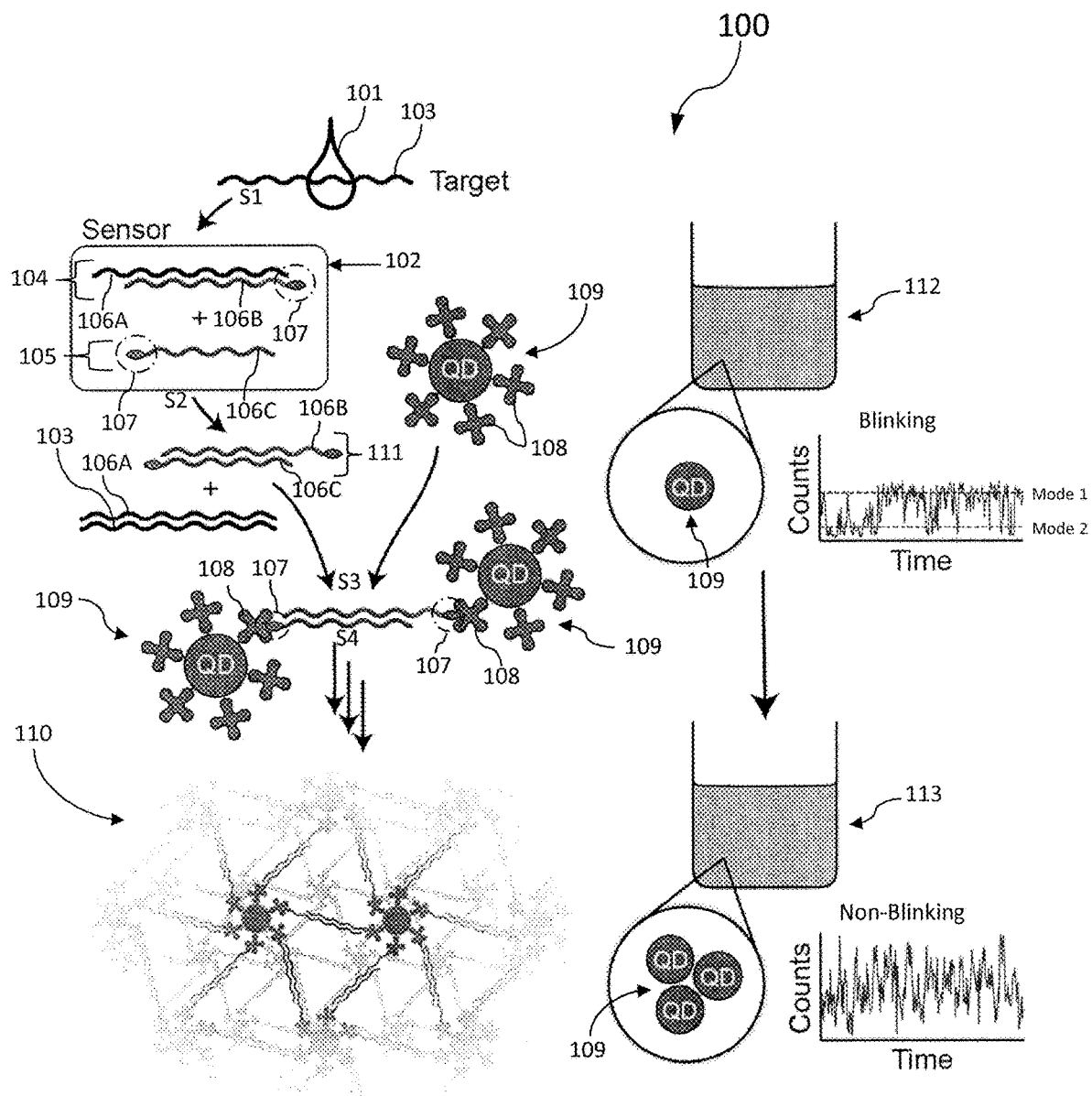
FIG. 1 is a schematic illustration of a biosensing composition and method according to one embodiment described herein.

Embodiments described herein can be understood more readily by reference to the following detailed description, examples and drawings and their previous and following descriptions. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Methods of Sensing

In one aspect, methods of sensing are described herein. In some embodiments, such a method comprises disposing a population of luminescent species in a test sample, exposing the test sample to electromagnetic radiation having a wavelength corresponding to an excitation wavelength of the luminescent species, detecting light emitted by the luminescent species within a detection region of the test sample, and correlating the light emitted by the luminescent species within the detection region to a presence or absence of an analyte within the test sample in an amount above a minimum detection threshold. Additionally, the luminescent species, in a non-aggregated state, exhibits luminescence blinking, or has a binary blinking luminescence profile. In an aggregated state, the luminescent species does not exhibit luminescence blinking, or has a continuous or quasi-continuous luminescence profile. Moreover, correlating the light emitted by the luminescent species to the presence or absence of the analyte comprises determining whether the light emitted by the luminescent species within the detection region is blinking luminescence or non-blinking luminescence. Further, in some preferred embodiments, the luminescent species of a method described above comprise colloidal quantum dots (QDs). In addition, in some cases, the analyte comprises a nucleic acid. However, luminescent species other than QDs and analytes other than nucleic acids may also be used.

For reference purposes herein, it is to be understood that, when a luminescent species (or population of luminescent species) is in a "non-aggregated state," any particular individual luminescent species is spatially separated from other luminescent species of the population of luminescent species by a distance sufficient to resolve the luminescence of the individual luminescent species during the light detection step of the method. That is, the individual luminescent species are "free" or isolated from one another. Moreover, as described further hereinbelow, a luminescent species in a non-aggregated state is generally not physically or chemically coupled or attached to another luminescent species of the population, particularly not at a shortest separation distance of less than 100 nm.

Further, a luminescent species that "exhibits luminescence blinking" in a non-aggregated state is to be understood to exhibit binary blinking, in which the individual luminescent species has alternating "on" times (or "on" states) and "off" times (or "off" states). As understood by one of ordinary skill in the art, such "on" times (or "on" states) correspond to times (or states) in which the luminescent species emits luminescence (e.g., fluorescence) when appropriately excited (e.g., by a beam of electromagnetic radiation having a wavelength corresponding to an excitation or absorption wavelength of the luminescent species). Similarly, "off" times (or "off" states) correspond to times (or states) in which the luminescent species does not emit luminescence (e.g., fluorescence), even when the luminescent species is appropriately excited (e.g., by the same excitation beam described above). Such binary blinking behavior of QDs, for instance, is described in Efros et al., "Random Telegraph Signal in the Photoluminescence Intensity of a Single Quantum Dot," *Phys. Rev. Lett.* 1997, 78, 1110-1113.

It is further to be understood, for reference purposes herein, that a luminescent species in an "aggregated state" is not in a "non-aggregated state" as described above. That is, individual luminescent species in an aggregated state are not spatially separated from one another by a distance sufficient to resolve the luminescence of the individual luminescent species during the light detection step of the method. Rather, the individual luminescent species are sufficiently close to one another that their individual luminescence profiles are not resolved and instead combine to form a composite or aggregate luminescence profile. Moreover, as described further hereinbelow, luminescent species in an aggregated state are generally physically or chemically coupled or attached to one another. For example, in some embodiments, luminescent species in an aggregated state are coupled or attached to one another at an average shortest separation distance of less than 100 nm, less than 50 nm, less than 30 nm, less than 20 nm, or less than 10 nm.

Further, it is to be understood that a luminescent species that "does not exhibit luminescence blinking" in an aggregated state does not exhibit binary blinking, in the aggregate. In other words, individual luminescent species may (and generally do) continue to exhibit binary blinking behavior even when aggregated with other individual luminescent species. But the aggregate itself does not exhibit such blinking behavior, particularly not for aggregates of at least 3, at least 4, or at least 5 individual luminescent species. Instead, the composite or aggregate luminescence profile of the luminescent species "in the aggregated state" exhibits non-blinking or quasi-continuous luminescence. That is, the composite or aggregate luminescence profile does not exhibit a binary pattern of alternating "on" times (or "on" states) and "off" times (or "off" states).

Therefore, determining whether the light emitted by the luminescent species within the detection region is blinking luminescence or non-blinking luminescence can be synonymous with determining whether the luminescent species is in a non-aggregated state (blinking luminescence observed) or an aggregated state (non-blinking luminescence observed). Accordingly, correlating the observation of a certain luminescence to the presence or absence of an analyte can be carried out by assigning the presence of the analyte to a specific luminescence type. For example, observation of non-blinking luminescence in an "assembly" approach can be assigned to the presence of an analyte, and observation of blinking luminescence can be assigned to the absence of the analyte. Similarly, in a "disassembly" approach, observation of blinking luminescence can be assigned to the presence of an analyte, and observation of non-blinking luminescence can be assigned to the absence of the analyte.

Again, for the sake of clarity, it is to be understood that such observed "blinking luminescence" or "non-blinking luminescence" refers to the total or overall luminescence emitted within and detected from the detection region during the detection step of a method described herein. Thus, if the luminescent species is in a non-aggregated state, the "blinking luminescence" corresponds to the luminescence of an individual, blinking luminescent species. Alternatively, if the luminescent species is in an aggregated state, the "non-blinking luminescence" corresponds to the luminescence of a collection, lattice, or aggregate of individual luminescent species, wherein the individual luminescent species may still be blinking but the total or overall luminescence of the collection, lattice, or aggregate does not display binary blinking behavior. Similarly, a "continuous" or "quasi-continuous" luminescence profile refers to a total luminescence signal that does not exhibit binary blinking behavior.

A "test sample," for reference purposes herein, is a sample that either contains an analyte of interest or that may possibly contain the analyte of interest. That is, a test sample is a sample to be tested for the presence of an analyte according to a method described herein. As understood by one of ordinary skill in the art, such a sample may or may not actually contain the analyte of interest. Such a sample may instead be believed to contain or believed to possibly contain the analyte of interest. Moreover, it is to be understood that the "analyte" of a method described herein is a species whose presence or absence in a sample is to be determined or tested for. Additionally, a test sample described herein can be a fluid or liquid sample, such as a solution, mixture, or colloid that contains an analyte (and possibly one or more additional, non-analyte species) or is believed to possibly contain the analyte (with or without one or more additional, non-analyte species). Further, in some cases, the analyte is dissolved or dispersed in the test sample, such that the test sample can be considered to be a solution or colloid of the analyte. Further, a test sample described herein, in some embodiments, is a chemical or biological environment, such as an in vivo environment or an in vitro environment.

Moreover, as described above, a method according to the present disclosure can be based on an "assembly" approach or a "disassembly" approach. For example, in some instances, the population of luminescent species, when initially disposed in the test sample, is in the non-aggregated state, and the presence of the analyte within the test sample causes the population of luminescent species to transition from the non-aggregated state to the aggregated state, resulting in detection of non-blinking luminescence. In such an aggregated state, an aggregate, collection, or lattice of individual luminescent species may be formed, wherein the aggregate, collection, or lattice of luminescent species includes at least 3, at least 4, or at least 5 individual luminescent species. Such an aggregate, collection, or lattice of luminescent species, in some embodiments, includes more than 5, more than 10, more than 20, more than 50, or more than 100 individual luminescent species. The number of individual luminescent species in an aggregate, collection, or lattice of luminescent species is not particularly limited, provided that the number is sufficiently large for the observation of non-blinking luminescence.

Further, in some such cases, one or more additional steps can be used to facilitate the assembly of a plurality of individual luminescent species. For instance, in some embodiments, a method described herein further comprises disposing an analyte binding species (or more than one analyte binding species) in the test sample prior to disposing the population of luminescent species in the test sample. The one or more analyte binding species, in the presence of the analyte, binds to the analyte and forms one or more coupling species or coupling agents. In the absence of the analyte, the analyte binding species does not form the coupling species. Moreover, the coupling species, when formed in the presence of the analyte, is operable to couple or aggregate a plurality of the luminescent species to one another. In some instances, the coupling species is operable to couple two of the luminescent species to one another. In other embodiments, the coupling species is operable to couple more than two of the luminescent species to one another. Further, in some cases, individual luminescent species of the population of luminescent species comprise one or more moieties for binding to the coupling species. As described further hereinbelow, it is also possible that the analyte itself, rather than a separate coupling species, couples or attaches luminescent species to one another. Moreover, in some cases, the presence of a single analyte molecule can result in the aggregation of more than two luminescent species. As described further hereinbelow, in some instances, the presence of a single analyte molecule causes the formation of a plurality of "dimers" of luminescent species (such as dimers consisting essentially of two QDs coupled to one another), or causes the formation of a single aggregate or lattice of luminescent species (such as QDs), wherein the number of individual luminescent species forming the aggregate or lattice is greater than two.

In some exemplary embodiments of a "disassembly" approach, the population of luminescent species, when initially disposed in the test sample, is in the aggregated state, and the presence of the analyte within the test sample causes the population of luminescent species to transition from the aggregated state to the non-aggregated state, resulting in detection of blinking luminescence. For example, in some such instances, individual luminescent species in the population of luminescent species in the aggregated state are coupled to one another by one or more analyte binding species, thereby defining coupled or aggregated individual luminescent species. Further, the one or more analyte binding species, in the presence of the analyte, preferentially binds to the analyte and unbinds from the coupled individual luminescent species, thereby decoupling the individual luminescent species from one another. However, in the absence of the analyte, the one or more analyte binding species does not substantially unbind from or decouple the coupled individual luminescent species from one another. Moreover, in some such cases, the one or more analyte binding species couples the individual luminescent species to one another via one or more coupling moieties of the individual luminescent species, as described further hereinbelow.

Specific steps of methods described hereinabove will now be further described in greater detail.

Methods described herein comprise disposing a population of luminescent species in a test sample. Any test sample not inconsistent with the objectives of the present disclosure may be used. For example, as described above, a test sample described herein can be a fluid or liquid sample, such as a solution, mixture, or colloid that contains an analyte (and possibly one or more additional, non-analyte species) or is believed to possibly contain the analyte (with or without one or more additional, non-analyte species). Further, in some cases, the analyte is dissolved or dispersed in the test sample, such that the test sample can be considered to be a solution or colloid of the analyte. Further, a test sample described herein, in some embodiments, is a chemical, biological, or non-biological environment. For instance, a biological environment may include an in vivo environment or an in vitro environment. In some cases, a biological environment comprises a healthy organ or healthy tissue. In other instances, a biological environment comprises a diseased organ or diseased tissue. A biological environment may also comprise a healthy or diseased cell or population of cells. In some embodiments, a biological environment comprises a blood vessel or the blood stream of a patient. A biological environment may also comprise a bodily fluid, bodily fluid stream, or bodily fluid vessel other than blood, a blood stream, or a blood vessel. For example, in some instances, a biological environment comprises sweat or urine, or a vessel or stream of sweat or urine. A chemical environment, in some cases, comprises or defines a non-biological aqueous environment. A chemical environment can also comprise or define an organic solution, colloid, or mixture, or a solid state environment. For example, in some instances, an environment is a solid state environment comprising or defined by a polymer or hydrogel. In some such embodiments, a luminescent species described herein is attached or conjugated to and/or immobilized in a polymer or oligomer backbone or hydrogel of the environment. Solid state, real-time analyte detection or monitoring can thus be provided by a method described herein. "Real-time," for reference purposes herein, indicates that detection may be performed at the same rate or at substantially the same rate as luminescent emission data is provided by the method, or, alternatively, that detection may be performed at the same time, or at substantially the same time, as luminescence occurs in an environment. For example, in some cases, real-time detection or monitoring occurs within 1 second, within 1 millisecond (ms), within 100 microseconds (µs), or within 10 µs of a corresponding occurrence of luminescence. In some instances, real-time detection or monitoring occurs at a rate that is within 1%, within 0.5%, or within 0.1% of a corresponding rate of provision of luminescence data, where the percentage is based on the larger rate.

Moreover, any luminescent species not inconsistent with the objectives of the present disclosure may be used. In some cases, the luminescent species comprise colloidal quantum dots. Any quantum dots not inconsistent with the objectives of the present invention may be used. Further, a "quantum dot," for reference purposes herein, comprises a semiconductor nanocrystal having a size in two or three dimensions that is sufficiently small to exhibit quantum confinement effects, particularly with respect to the bandgap energy of the quantum dot. Thus, a quantum dot can be a semiconductor nanocrystal having a length two or three dimensions that is no greater than about two times the exciton Bohr radius of the semiconductor material forming the quantum dot. In some cases, a quantum dot described herein has a length in two or three dimensions of about 1-50 nm, 1-30 nm, 1-20 nm, or 1-15 nm.

Quantum dots described herein may also be substantially monodisperse or have a narrow size distribution. For example, in some cases, the size distribution of a population of QDs described herein has a standard deviation of less than about 15%, less than about 10%, or less than about 8%. In some instances, the standard deviation is about 5-15%, 5-10%, or 8-15%.

Additionally, "colloidal" QDs can be formed through a solution-based nucleation and growth mechanism, rather than through a molecular beam nucleation and growth mechanism, such as a molecular beam epitaxy (MBE) mechanism. Moreover, a "colloidal" QD can include a "ligand" shell comprising a plurality of "ligands," "caps," or "capping molecules" attached to at least a portion of the exterior surface of the QD. Such ligands or caps can provide steric and/or thermodynamic hindrance to the coalescence or fusing of individual QDs, and may also permit the QDs to be dispersed or dissolved in a solvent. Additionally, the ligands or caps of a QD may be attached or bonded to the exterior surface of the QD through a covalent or non-covalent bond. For example, in some cases, ligands are bonded to the exterior surface of the QD through one or more dative bonds. Non-limiting examples of ligands that may form a ligand shell of a colloidal QD described herein include phosphines, phosphine oxides, amines, thiols, carboxylates, and carboxylic acids. Further, such ligands can be monodentate or multidentate, and monomeric or dendrimeric. Ligands of a colloidal QD may also include 4 to 50, 4 to 30, or 4 to 20 carbon atoms, including as part of one or more aliphatic "tails" or chains, such as included in a trioctylphosphine ligand. Moreover, as described further hereinbelow, one or more caps or ligands of a QD can serve to couple the QD to an analyte binding species or coupling species. In some embodiments, one or more nucleic acids can form or define one or more ligands of a QD described herein, including as an analyte binding species.

In some cases, QDs described herein are formed from a Group II-VI semiconductor material such as ZnS, ZnSe, ZnTe, CdS, CdSe, CdTe, HgS, HgSe, or HgTe. Additionally, QDs described herein, in some embodiments, can be formed from a mixture, blend, or alloy of one or more of the foregoing Group II-VI semiconductor materials, such as $Cd_xZn_{(1-x)}S$. In other instances, QDs described herein are formed from a Group III-V semiconductor material such as GaN, GaP, GaAs, GaSb, InP, InAs, or InSb, or from a mixture, blend, or alloy of one or more of the foregoing Group III-V semiconductor materials, such as $InP_xAs_{(1-x)}$).

Moreover, in some embodiments, a QD described hereinabove further includes a dopant. Further, such a dopant can be an emissive dopant. For example, in some instances, a QD described herein is formed from a Group II-VI semiconductor material or a Group III-V semiconductor material doped with one or more of Mn, Fe, Co, Ni, Pd, Pt, Cu, Al, Ag, Au, and a rare earth metal.

Additionally, in some cases, QDs described herein comprise core/shell QDs. As understood by one of ordinary skill in the art, "core/shell" QDs comprise a "core" formed from a first semiconductor material overcoated or surrounded by a "shell" formed from a second semiconductor material. The first and second semiconductor materials can be different materials. In some cases, the second semiconductor material has a higher bandgap than the first semiconductor material and the band energies of the first semiconductor material lie within the band energies of the second semiconductor material. In such a "Type I" configuration, quantum confinement of the exciton can take place primarily within the core. Core/shell QDs may also have a "Type II" configuration in which the bands of the core and shell are "offset" such that one type of carrier (e.g., the electron) may be primarily confined to one portion of the QD (e.g., either the core or the shell), and the other type of carrier (e.g., the hole) may be primarily confined to another portion of the QD (e.g., the shell or the core), such that the Type II QD exhibits an effective bandgap smaller than the bandgap of either the core or the shell. A QD described herein may also have more than one shell. For example, in some cases, a QD described herein is a core/shell/shell QD. Other configurations are also possible, and methods described herein are not particularly limited to a specific QD structure. Some non-limiting examples of core/shell QDs that may be suitable for use in some embodiments described herein include CdS/ZnS, CdS/ZnSe, CdS/ZnTe, CdSe/ZnS, CdSe/ZnSe, CdSe/ZnSe, CdSe/CdS, InAs/InP, and InAs/ZnSe.

Further, the semiconductor material or materials and/or the structure of a QD described herein may be selected to provide a desired photoluminescent emission profile. For example, in some cases, the QDs described herein emit electromagnetic radiation centered in, or having a peak or average emission in, the visible region of the electromagnetic spectrum. In some such cases, the QDs emit electromagnetic radiation having a peak or average emission between about 350 nm and 650 nm, between about 400 nm and 620 nm, between about 450 nm and 650 nm, between about 450 nm and 600 nm, between about 500 nm and 650 nm, between about 500 nm and 620 nm, between about 500 nm and 600 nm, between about 520 nm and 600 nm, between about 525 nm and 535 nm, between about 550 nm and 600 nm, between about 570 nm and 600 nm, or between about 580 nm and 590 nm. Alternatively, in other instances, QDs described herein emit electromagnetic radiation having a peak or average emission in the near infrared (NIR, 750 nm-1.4 μm) or ultraviolet A (UVA, 315-400 nm) portion of the electromagnetic spectrum.

Moreover, QDs described herein can have a high internal photoluminescent quantum yield (QY). In some embodiments, QDs described herein have an internal photoluminescent QY of up to 70%, up to 60%, up to 50%, up to 40%, or up to 30%. In some instances, QDs described herein have an internal photoluminescent QY of 10-70%, 10-60%, 10-40%, 15-70%, 15-60%, 15-50%, 15-40%, 20-70%, 20-50%, 20-40%, 30-70%, or 30-50%.

A luminescent species described herein can also be an organic fluorophore or an organic dye that exhibits blinking, including binary blinking as described above. Such a luminescent species may include a fluorescent protein such as green fluorescent protein (GFP) or yellow fluorescent protein (YFP), or a cyanine dye such as Cy5.

Further, a luminescent species described herein may be disposed in the test sample in any manner not inconsistent with the objectives of the present disclosure. In some cases, for example, a luminescent species or population of luminescent species described herein is disposed in a test sample (such as a biological compartment) by injecting the composition into the sample (or compartment) directly or indirectly, such as may be achieved by subcutaneous injection or injection into vasculature of a mammal. A luminescent species described herein may also be disposed in a test sample (such as a biological compartment of a mammal) by topical application of the luminescent species to a surface of skin or other surface of the mammal. In some cases, a luminescent species described herein is disposed in a biological compartment by diffusion of the composition into the compartment. Other methods of disposing a luminescent species in a test sample may also be used Methods described herein also comprise exposing the test sample to electromagnetic radiation having a wavelength corresponding to an excitation wavelength of the luminescent species. The test sample can be exposed to electromagnetic radiation in any manner not inconsistent with the objectives of the present disclosure. In some cases, for instance, a laser excitation source is used. In other embodiments, a non-laser light emitting diode or a broad band light (BBL) excitation source is used. Further, the excitation wavelength can be in any region of the electromagnetic spectrum suitable to excite a chosen luminescent species. In some embodiments, the excitation wavelength is in the ultraviolet (UV) region (e.g., between 100 nm and 350 nm) or visible region (e.g., between 350 nm (or 351 nm) and 800 nm) of the electromagnetic spectrum.

Methods described herein also comprise detecting light emitted by the luminescent species within a detection region of the test sample. Such a detection step can be carried out in any manner not inconsistent with the objectives of the present disclosure. For example, photoluminescence signals or emitted light of a method described herein can be detected using any detector configuration not inconsistent with the objectives of the present disclosure. In some embodiments, for instance, emitted light is detected using a camera or photon counter. In some cases, emitted light may be detected using a detector comprising a plurality of optical fiber collectors coupled to a camera or photon counter, such as a charge coupled device (CCD) or a photomultiplier tube (PMT). Further, in some embodiments, the optical fiber collectors are spatially distributed around the test sample or around a detection surface of the test sample (such as skin or another exterior surface of a biological environment). Any desired number of optical fiber collectors can be used. In some embodiments, up to 30, up to 20, or up to 10 optical fiber collectors are used. In some cases, 4-30, 4-20, 6-30, 6-20, 8-30, 8-20, 10-30, or 10-20 optical fiber collectors are used. Other configurations are also possible. Moreover, in some instances, emitted light is detected using fluorescence correlation spectroscopy (e.g., in solution) or a confocal microscope, such as a confocal fluorescence microscope (e.g., in the solid state or on a substrate). Additionally, in some such cases, the detection region of the method corresponds to a focal region, area, or volume of the confocal microscope. In other instances, the detection region of the method corresponds to a region, area, or volume from which emitted light is received by a detector described herein and/or a region, area, or volume that is excited by an excitation beam described herein.

Moreover, in some cases, a plurality of luminescence signals or emitted light at a plurality of locations within a test sample is detected by raster scanning the test sample. Such raster scanning can include raster scanning of one or more excitation beams across or within the test sample, such that the excitation beam sequentially generates a series of detection regions at different locations within the test sample. It is also possible, in some instances, to move or scan a detector described herein from location to location within the test sample. Moving or scanning a detector in such a manner can increase the detection area of the method. In other cases, a two-dimensional detector such as a charge-coupled device (CCD) image sensor or camera is used to detect photoluminescence signals or emitted light at a plurality of locations simultaneously.

Methods described herein also comprise correlating the light emitted by the luminescent species within the detection region to a presence or absence of an analyte within the test sample in an amount above a minimum detection threshold.

"Correlating," as used herein, does not necessarily refer to mathematical correlation, such as mathematical correlation of variables. Instead, "correlating" refers to using one or more properties or characteristics of the light emitted by the luminescent species to identify whether one or more analytes is present or absent within the test sample, or to identify a concentration of one or more analytes within the test sample. Specific examples and/or embodiments demonstrating a correlating step are described further herein below. However, it is generally to be understood that a correlating step can include using a temporal profile or trace of the light emitted by the luminescent species within the detection region (e.g., as compared against a baseline or "control" level) to determine whether an analyte is present or absent within a test sample. In particular, the presence or absence of "blinking" behavior (including binary blinking behavior), as opposed to non-blinking, continuous, or quasi-continuous behavior, can be used in a correlating step described herein. The minimum detection threshold of a method described herein can be an analyte concentration as low as $10^{-12}$ molar (M). In some embodiments, the minimum detection threshold is $10^{-12}$ M to $10^{-6}$ M, $10^{-9}$ M to $10^{-6}$ M, or $10^{-6}$ M to $10^{-3}$ M. In some cases, the minimum detection threshold is 0.001 to 10 ppm, 0.01 to 10 ppm, 0.1 to 10 ppm analyte, or 1 to 10 ppm analyte.

Further, a method described herein can be used to detect or sense any analyte not inconsistent with the objectives of the present disclosure. In some cases, the analyte comprises a nucleic acid. In some embodiments, nucleic acid comprises ribonucleic acid (RNA). In other cases, nucleic acid comprises deoxyribonucleic acid (DNA). Further, the RNA and/or DNA can comprise any type of RNA and/or DNA not inconsistent with the objectives of the present disclosure. In some embodiments, for instance, RNA comprises mRNA, rRNA, tRNA, siRNA, or combinations or mixtures thereof. DNA, in some cases, comprises A-DNA, B-DNA, Z-DNA, cDNA or combinations or mixtures thereof. Additionally, in some instances in which an analyte is a nucleic acid, the nucleic acid has a length of at least about 20 bases or base pairs. Not intending to be bound by theory, it is believed that analytes having such minimal lengths can bind to other species with favorable thermodynamics, as described further below. Other analytes may also be detected or sensed using a method described herein. For example, in some instances, the analyte comprises one or more non-nucleic acid biomolecules, such as one or more of proteins (including naturally occurring proteins or engineered proteins), antibodies, antibody fragments, peptides, and small molecules. An analyte may also comprise a ribozyme or aptamer.

Additionally, in some embodiments, methods described herein further comprise disposing an analyte binding species or agent in the test sample prior to disposing the population of luminescent species in the test sample, or otherwise using an analyte binding species or agent. Methods described herein can also comprise forming or otherwise using a coupling species or agent. Any such analyte binding species and/or coupling species not inconsistent with the objectives of the present disclosure may be used. Moreover, it is to be understood that an "analyte binding species" or "analyte binding agent" refers to a species that is operable to bind to an analyte described herein (or to one or more portions or moieties of the analyte). In some cases, the analyte binding agent binds to an analyte (or portion thereof) in a selective manner or with a higher binding strength or binding energy than the analyte binding species binds to other species present, and/or with a higher binding strength or binding energy than the analyte (or portion thereof) binds to other species present. Moreover, as described further hereinbelow, in some cases, the relative binding energies of various possible "binding pairs" present in a method at a given time favor the formation of specific binding pairs or bonding outcomes. For instance, in some cases, the relevant binding energies thermodynamically favor the formation of a coupling species described herein, or favor the decoupling of an aggregate of individual luminescent species described herein.

Similarly, a "coupling species" or "coupling agent" refers to a species that couples, joins, connects, or attaches (or is operable to couple, join, connect, or attach) a plurality of individual luminescent species to one another.

As described herein, analyte binding species, coupling species, and/or luminescent species can include one or more reactive moieties or functional groups that can serve to bond or couple various components or species to each other. Such moieties or functional groups may also be referred to herein as coupling moieties. Such moieties or functional groups can include any chemical moieties or functional groups not inconsistent with the objectives of the present disclosure. In general, such moieties or functional groups are operable to react with one another (including, in certain embodiments, in a selective manner) to accomplish a desired binding or coupling described herein. In some cases, such a moiety or functional group includes a clickable moiety (that is, a moiety that can participate in a "click chemistry" reaction, such as an azide or alkyne moiety). A coupling moiety or functional group can also comprise a nucleic acid segment, protein, antibody, antibody fragment, or peptide. In some cases, a coupling moiety or functional group comprises a minibody, diabody, triabody, tetrabody, aptamer, affibody, or peptoid. Additional non-limiting examples of coupling moieties or functional groups useful in some embodiments described herein for coupling purposes include streptavidin, biotin, anti-PSMA, $NH_2GR_{11}$, and c(RGDyK). Moreover, as understood by one of ordinary skill in the art, moieties or functional groups described herein as selectively coupling to one another can comprise "pairs" of moieties or functional groups known or designed to selectively interact with one another, such as pairs of complementary single-stranded nucleic acid, pairs of clickable moieties (e.g., an azide moiety paired with an alkyne moiety), or streptavidin paired with avidin or biotin.

Exemplary embodiments of methods described herein are further described in the specific Examples below. Additionally, with reference to the Examples section, exemplary "assembly" based methods can be described as follows.

As described herein, in "assembly" based embodiments, the population of luminescent species of a method described herein, when initially disposed in a test sample, is in the non-aggregated state. Further, the presence of the analyte within the test sample causes the population of luminescent species to transition from the non-aggregated state to the aggregated state, resulting in detection of non-blinking luminescence. In some such cases, the method further comprises disposing an analyte binding species in the test sample prior to disposing the population of luminescent species in the test sample. The analyte binding species, in the presence of the analyte, binds to the analyte and forms a coupling species. Moreover, the analyte binding species, in the absence of the analyte, does not form the coupling species. Further, the coupling species, which is formed in the presence of the analyte, is operable to couple a plurality of the luminescent species to one another. In some such embodiments, the luminescent species, in the non-aggregated state, comprise colloidal quantum dots having one or more first coupling moieties attached to exterior surfaces of the colloidal quantum dots, and the analyte comprises a single-stranded analyte nucleic acid. Additionally, the analyte binding species comprises a double-stranded nucleic acid consisting of a single-stranded guard nucleic acid bound to a single-stranded anti-guard nucleic acid. The anti-guard nucleic acid has a terminus comprising a toehold nucleic acid segment and comprising a second coupling moiety that is operable to selectively bind to the one or more first coupling moieties of the colloidal quantum dots. The guard nucleic acid is operable to bind to the analyte nucleic acid. Further, the anti-guard nucleic acid is operable to bind to a single-stranded complementary anti-guard nucleic acid. The complementary anti-guard nucleic acid has a terminus comprising a third coupling moiety that is operable to selectively bind to the one or more first coupling moieties of the colloidal quantum dots. Moreover, the coupling species comprises a double-stranded nucleic acid consisting of the anti-guard nucleic acid bound to the complementary anti-guard nucleic acid such that the second coupling moiety and the third coupling moiety are on opposite terminuses of the coupling species. Further, in some exemplary embodiments, binding energies of (a) the analyte nucleic acid to the guard nucleic acid, (b) the guard nucleic acid to the anti-guard nucleic acid, and (c) the anti-guard nucleic acid to the complementary anti-guard nucleic acid thermodynamically favor formation of the coupling species. In addition, in some cases, the one more first coupling moieties comprise streptavidin, and the second coupling moiety and the third coupling moiety comprise biotin or avidin.

In another exemplary embodiment according to the "assembly" approach, the luminescent species, in the non-aggregated state, comprise a colloidal quantum dot (CQD) having a first single-stranded nucleic acid (1), a second single-stranded nucleic acid (2), and a third single-single stranded nucleic acid (3) attached to an exterior surface of the CQD. Further, the analyte comprises a single-stranded analyte nucleic acid having a first binding moiety (p1'), a second binding moiety (p2'), and a third binding moiety (p3'). The analyte binding species comprises a first single-stranded nucleic acid (p1) bound to a first complementary single-stranded nucleic acid (1') attached to a first quantum dot (QD1), a second single-stranded nucleic acid (p2) bound to a second complementary single-stranded nucleic acid (2') attached to a second quantum dot (QD2), and a third single-stranded nucleic acid (p3) bound to a third complementary single-stranded nucleic acid (3') attached to a third quantum dot (QD3). Moreover, (p1') is operable to bind to (p1), (p2') is operable to bind to (p2), (p3') is operable to bind to (p3), (1') is operable to bind to (1), (2') is operable to bind to (2), and (3') is operable to bind to (3). Additionally, the coupling species of this exemplary method comprises a species in which (1') is bound to (1), (2') is bound to (2), and (3') is bound to (3). Further, binding energies of (p1') bound to (p1), (p2') bound to (p2), (p3') bound to (p3), (1') bound to (1), (2') bound to (2), and (3') bound to (3) thermodynamically favor formation of the coupling species.

Similarly, again with reference to the Examples section, an exemplary "disassembly" based method can be described as follows. First, it is to be understood that, in this exemplary method, the population of luminescent species, when initially disposed in the test sample, is in the aggregated state. Further, the presence of the analyte within the test sample causes the population of luminescent species to transition from the aggregated state to the non-aggregated state, resulting in detection of blinking luminescence. Additionally, individual luminescent species in the population of luminescent species in the aggregated state are coupled to one another by one or more analyte binding species. The one or more analyte binding species, in the presence of the analyte, preferentially binds to the analyte and unbinds from the coupled individual luminescent species, thereby decoupling the individual luminescent species from one another. Further, the one or more analyte binding species, in the absence of the analyte, does not substantially unbind from or decouple the coupled individual luminescent species from one another. In some exemplary embodiments according to the foregoing, the coupled individual luminescent species comprise a colloidal quantum dot (CQD) bound to a first additional quantum dot (QD1), a second additional quantum dot (QD2), and a third additional quantum dot (QD3). The CQD has a first single-stranded nucleic acid (1), a second single-stranded nucleic acid (2), and a third single-single stranded nucleic acid (3) attached to an exterior surface of the CQD. Additionally, the analyte binding species comprise a first single-stranded nucleic acid (p1) bound to a first complementary single-stranded nucleic acid (1') attached to the QD1 and to (1), a second single-stranded nucleic acid (p2) bound to a second complementary single-stranded nucleic acid (2') attached to the QD2 and to (2), and a third single-stranded nucleic acid (p3) bound to a third complementary single-stranded nucleic acid (3') attached to the QD3 and to (3). The analyte comprises a single-stranded analyte nucleic acid having a first binding moiety (p1'), a second binding moiety (p2'), and a third binding moiety (p3'). Moreover, binding energies of (p1') bound to (p1), (p2') bound to (p2), (p3') bound to (p3), (1') bound to (1), (2') bound to (2), and (3') bound to (3) thermodynamically favor the decoupling of the QD1, the QD2, and the QD3 from the CQD.

The foregoing exemplary embodiments of "assembly" based and "disassembly" based methods described herein are further illustrated in the specific Examples below. It is further to be understood that additional exemplary embodiments, in which different "analyte binding species" and/or "coupling species" are used, are also described in the specific Examples hereinbelow. Such additional embodiments can be understood and described as variations of the more general "assembly" and "disassembly" approaches, where the precise "analyte binding species" and/or "coupling species," if present, vary.

II. Sensing Compositions

In another aspect, sensing compositions are described herein. As with methods of sensing described in Section I above, sensing compositions described herein can be used to sense or detect an analyte by "assembly" of individual luminescent species of the composition, or by "disassembly" of individual luminescent species of the composition. For example, in some embodiments, a composition described herein comprises a population of individual luminescent species, wherein the luminescent species, in a non-aggregated state, exhibits luminescence blinking, or has a binary blinking luminescence profile. In an aggregated state, the luminescent species does not exhibit luminescence blinking, or has a continuous or quasi-continuous luminescence profile. Further, the individual luminescent species are operable to transition from the non-aggregated state to the aggregated state in the presence of an analyte, including in a manner described hereinabove in Section I. Alternatively, in other cases, a sensing composition described herein comprises a coupled or aggregated luminescent species formed from a collection, lattice, or aggregate of individual luminescent species. The individual luminescent species, in a non-aggregated state, exhibit luminescence blinking and, in an aggregated state, are non-blinking or do not exhibit luminescence blinking. Moreover, the coupled luminescent species is operable to transition from the aggregated state to the non-aggregated state in the presence of an analyte, including in a manner described hereinabove in Section I. Additionally, in some preferred embodiments of sensing compositions described herein, the individual luminescent species comprise colloidal quantum dots. Moreover, sensing compositions described herein, in some cases, further comprise one or more additional components, such as one or more analyte binding species and/or one or more coupling species. It is to be understood that such additional species can comprise any analyte binding species or coupling species described hereinabove in Section I.

Specific components of sensing compositions described herein will now be further described in more detail.

Sensing compositions described herein comprise a population of luminescent species, or a coupled luminescent species formed from a collection, lattice, or aggregate of individual luminescent species. Any individual luminescent species not inconsistent with the objectives of the present disclosure may be used in a composition described herein. More particularly, any individual luminescent species described hereinabove in Section I may be used in a composition described herein. For example, in some preferred embodiments, the individual luminescent species comprise colloidal QDs, including colloidal QDs described hereinabove in Section I.

Further the "aggregated" and "non-aggregated" states, and the "blinking" or "non-blinking" characteristics of the luminescent species, are to be understood in the same manner as described hereinabove in Section I. Similarly, the individual (or coupled) luminescent species can transition from the non-aggregated state to the aggregated state (or from the aggregated to the non-aggregated state) in the presence of any analyte not inconsistent with the objectives of the present disclosure. More particularly, the analyte can be any analyte described hereinabove in Section I. For instances, in some embodiments, the analyte is a nucleic acid.

In some cases, sensing compositions described herein further comprise one or more analyte binding species and/or one or more coupling species. Any such species not inconsistent with the objectives of the present disclosure may be used. Particularly, such species can comprise any analyte binding species or coupling species described hereinabove in Section I. For instance, in some embodiments, the analyte binding species comprises a nucleic acid.

Additional embodiments of sensing compositions and methods will now be further described with reference to the following non-limiting examples.

Example 1

Compositions and Methods for Sensing

In this Example, all biosensor oligos were purchased from Integrated DNA Technologies (IDT), Inc. All assemblies and reassociation experiments were analyzed by nondenaturing polyacrylamide gel electrophoresis (native-PAGE). Formation of QD-based lattices was analyzed with agarose gels. The QD-biosensor compositions solutions were analyzed by laser scanning confocal microscopy. Excitation was provided by a PicoQuant PDL 800-B pulsed laser with an LDH Series 470 nm laser head at a 10 MHz repetition frequency and power of 1.15 µW. Excitation pulses were coupled into a single-mode optical fiber, then directed to a 500 nm cutoff dichroic beam splitter before being focused onto the sample by a Zeiss 100×1.25 NA oil immersion objective lens.

FIG. 1 schematically illustrates aspects of a biosensor system 100 in which the presence or absence of an analyte is determined based on whether the light emitted by a luminescent species of a biosensor 102 is blinking luminescence (a luminous intensity range exhibiting binary blinking) or non-blinking luminescence (continuous fluctuations exhibited over a broader luminous intensity range being devoid of perceptible binary blinking) Quantum dots (QDs), also "QD" in the FIGs., are colloidal luminescent nanoparticles by which blinking luminescence or non-blinking luminescence is used to indicate the presence or absence of an analyte comprising one or more target or analyte strands or molecules. Binary, blinking luminescence is observable and/or perceptible when the one or more QDs are in a non-aggregated state whereas non-binary, quasi-continuous and/or non-blinking luminescence is observable and/or perceptible when two or more QDs are in an aggregated state. Biosensors configured to indicate the presence or absence of analyte based on its light emission scheme (e.g., as blinking or non-blinking) are advantageous, as the sensors do not require the analyte to induce fluorescence intensity or color changes making it readily applicable to a wide range of analyte species.

System 100 comprises a test sample 101 and a biosensor composition 102 (which also includes QDs 109, as described below) configured to test the sample 101 by indicating the presence or absence of a target species or analyte 103, as the sample 101 may or may not contain analyte 103. The biosensor 102 can comprise a solid, liquid, or gas phase testing medium configured to indicate the presence of absence of analyte 103. The analyte 103 can comprise one or more nucleic acids or another species that is not a nucleic acid. As noted above, a wide range of analytes and/or analyte species may be tested via the biosensor compositions 102 since the analyte 103 is not required to induce luminescent changes in the QDs. As FIG. 1 indicates, in some embodiments, the analyte 103 is a single-stranded nucleic acid.

At Step 1 (S1), the test sample 101 and biosensor composition 102 (not counting the QD portion, 109) are introduced to each other. This may occur via mixing, dropping, dissolving, dispersing, titrating, blending, stirring, or otherwise combining the test sample 101 and biosensor composition 102. Any other method of introducing the test sample 101 to the biosensor composition 102 not inconsistent with the instant application can be used to cause or induce species present in the biosensor composition 102 to intermingle with species present in the test sample 101. In some embodiments, the biosensor composition 102 triggers the aggregation, non-aggregation, or de-aggregation of QDs 109 (luminescent species), which indicates the presence or absence of analyte 103 based on whether the QD light emission is blinking or quasi-continuous and substantially non-blinking.

The biosensor composition 102 comprises an analyte binding species 104, a complementary coupler formation species 105, and one or more QDs 109. The analyte binding species 104 is a double-stranded nucleic acid consisting of a first single-stranded species 106A (also referred to as a guard nucleic acid) and a second single-stranded species 106B (also referred to as an anti-guard nucleic acid). At least one of the first and second single-stranded species 106A, 106B comprises a coupling moiety 107 that is operable to selectively bind to one or more binding sites 108 disposed on the QDs 109. The coupler formation species 105 comprises a third single-stranded species 106C with a coupling moiety 107 disposed thereon.

At S2, a DNA strand-displacement method is employed, during which the second single-stranded species 106B and the third single-stranded species 106C self-assemble to form a coupling species 111. During the strand-displacement method at S2, the first single-stranded species 106A further binds to the analyte 103.

At S3, the biosensor composition 102 thermodynamically drives the reassociation of DNA strands assisted by toeholds and coupling moieties 107 on the single-stranded DNA species. The reassociation of second and third single-stranded species 106B and 106C forms a coupling species 111 comprising double biotinylated DNA duplexes. The coupling species 111 rapidly cross-links the streptavidin-decorated QDs 109 to form a QD lattice 110 at S4. The biosensor coupling species 111 forms in the presence of analyte 103, which triggers formation of the QD lattice 110 via cross-linking the QDs 109. The coupling moieties 107 of coupling species 111 have a strong affinity for binding to the QD binding sites 108. In some embodiments, the coupling moieties 107 comprise biotin or avidin and the binding sites 108 comprise streptavidin. The presence of analyte 103 in the test sample 101 causes the population of QDs 109 to transition from a non-aggregated state to an aggregated state at S3 and S4 thus forming a lattice 110 of cross-linked QDs 109. When exposed to electromagnetic radiation at an excitation wavelength and/or range thereof, the QD lattice 110 emits light that is quasi-continuous and non-blinking or substantially non-blinking. Accordingly, the presence or absence of analyte can be determined and/or inferred using confocal fluorescence microscopy to detect a change in fluorescence trajectory from which the number of particles in the resulting lattice 110 may also be estimated.

Still referring to FIG. 1, a first test sample 112 comprises one or more non-aggregated QDs 109 and a second test sample 113 comprises one or more aggregated QDs 109. The isolated QD 109 in the first test sample 112 emits blinking luminescence for indicating the presence or absence of analyte and the aggregated QDs 109 in the second sample 113 emit non-blinking (quasi-continuous) luminescence for indicating the presence or absence of analyte. The presence of analyte 103 within a given test sample can cause the QDs 109 to transition from the non-aggregated state to the aggregated state (e.g., at steps S3, S4), resulting in detection of non-blinking luminescence. Notably, in some embodiments, the QDs 109 fail to aggregate in the absence of analyte 103 and have a blinking luminescence indicative of the absence of analyte 103. As FIG. 1 illustrates, the blinking luminance associated with single or non-aggregated QDs is bimodal over time (i.e., mode 1, mode 2 in the upper plot), which indicates the emitted light as being "off" and "on", or vice versa. In contrast, the light emitted by aggregated QDs (lower plot) results in a continuous light emission that can readily be distinguished (e.g., visually or optically) from blinking light, and is thus characterized as non-blinking light.

Figure 2A:
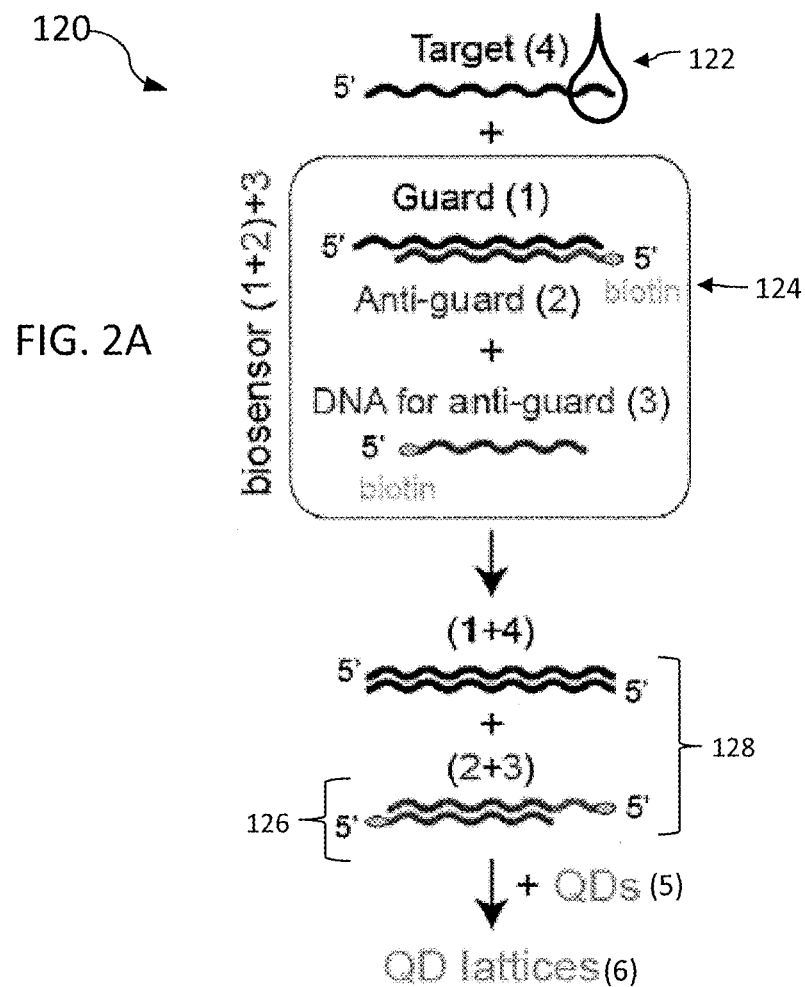
FIG. 2A is a schematic illustration of a biosensing composition and method according to one embodiment described herein.

FIG. 2A schematically illustrates a further embodiment of a biosensor system, generally designated 120. The system 120 comprises a test sample 122 and a biosensor composition 124. The biosensor composition 124 comprises a single-stranded guard nucleic acid 1, a single-stranded anti-guard nucleic acid 2, and a complementary anti-guard nucleic acid 3. The system 120 may or may not comprise a target molecule or analyte 4 comprising a target molecule. In the presence of analyte 4, the biosensor composition 124 can trigger the QDs 5 to either blink or not blink via the respective de-coupling or coupling of QDs 5. In FIG. 2A, analyte 4 is present. The presence of analyte 4 induces formation of a coupling species 126. The coupling species 126 is operable to couple or aggregate the plurality of QDs 5, which triggers formation of a QD lattice 6 resulting in non-blinking light emission. In the absence of analyte 4, the QDs 5 remain uncoupled resulting in blinking light emission.

The guard nucleic acid 1 and anti-guard nucleic acid 2 form an analyte binding species. The anti-guard nucleic acid 2 has a terminus comprising a toehold nucleic acid segment and a coupling moiety that is operable to selectively bind to one or more coupling moieties of the colloidal QDs 5. The coupling moiety in FIG. 2A is biotin. The complementary anti-guard nucleic acid 3 also has a terminus comprising a coupling moiety that is operable to selectively bind to one or more coupling moieties of the colloidal QDs 5. During reassociation at 128, the guard nucleic acid 1 binds to the analyte 4 (see, e.g., 1+4) and the anti-guard nucleic acid 2 binds to the complementary anti-guard nucleic acid 3 (see, e.g., 2+3). The anti-guard nucleic acid 2 and the complementary anti-guard nucleic acid 3 collectively form the coupling species 126 which triggers formation of QD lattice 6. Binding energies of the analyte nucleic acid 4 to the guard nucleic acid 1, the guard nucleic acid 1 to the anti-guard nucleic acid 2, and the anti-guard nucleic acid 2 to the complementary anti-guard nucleic acid 3 thermodynamically favor formation of the coupling species 126.

When the analyte 4 interacts with the guard nucleic acid 1, the biotinylated anti-guard nucleic acid 2 is released and reassociated with the complementary anti-guard nucleic acid 3 to form the coupling species 126 comprising a duplex with two biotins. The biotins of coupling species 126 cross-link the streptavidin of QDs 5, yielding QD lattices 6.

The free energies of the various structures were calculated to be −77 kcal/mol for the (1+2) duplex; −65 kcal/mol for the (2+3) duplex; and −97 kcal/mol for the (1+4) duplex. The difference of −12 kcal/mol prevents the (2+3) duplex formation in the biosensor composition 124; however, the presence of analyte 4 makes the formation of coupling species 126 more favorable, by about −85 kcal/mol, due to association and binding with analyte at (1+4).

Figure 2B:
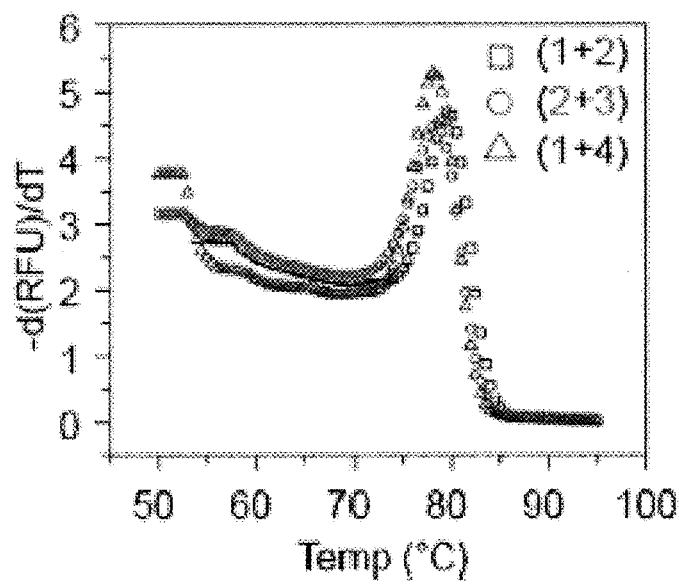
FIG. 2B illustrates melting temperature data associated with sensing compositions according to some embodiments described herein.

The melting temperatures shown in FIG. 2B for all duplexes were measured to be 79.5° C. (predicted 77.8° C.) for the (1+2) duplex, 78.5° C. (predicted 76.3° C.) for the (2+3) duplex, and 78° C. (predicted 78° C.) for the (1+4) duplex. The measured melting temperatures are in agreement with the predicted values (shown in parentheses).

Figure 2C:
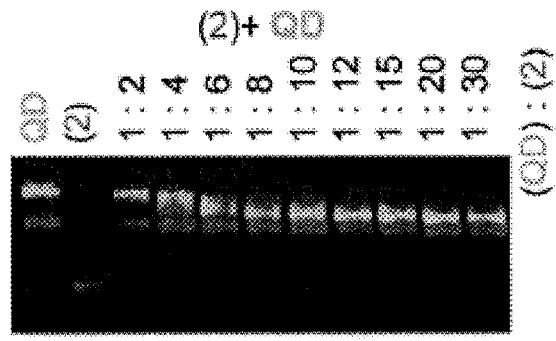
FIGS. 2C-2J each depict electrophoretic mobility shift assay data for sensing compositions according to some embodiments described herein.

Multiple electrophoretic mobility shift assays were provided, prior to blinking analysis, to verify the working principle of the biosensor system 120. First, as FIG. 2C illustrates, titration experiments showed that the maximum number of streptavidin-biotin interactions per QD was about 15-30. Due to the increase of overall negative charge of QDs upon DNA binding, their migration rate increases dramatically. However, the formation of lattices makes it difficult for QDs to enter the agarose gel because of size limitations.

Figure 2D:
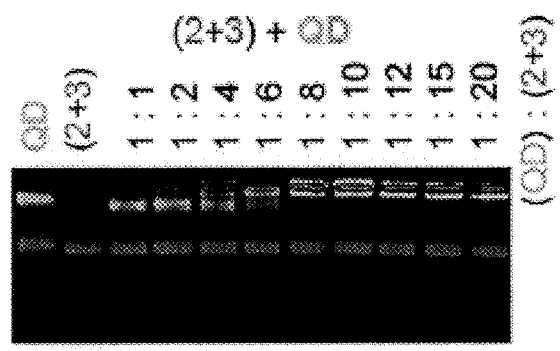
Figure 2E:
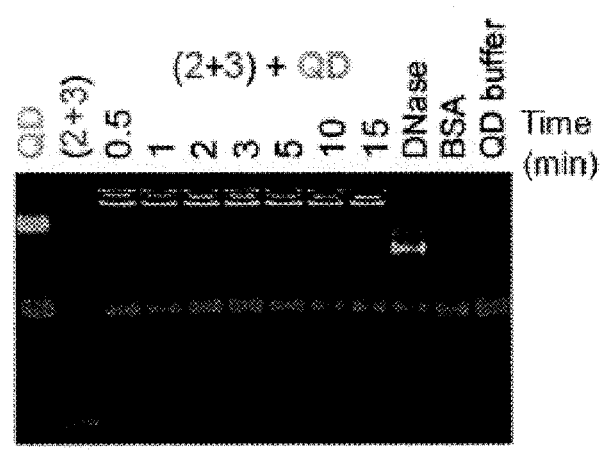
Figure 2F:
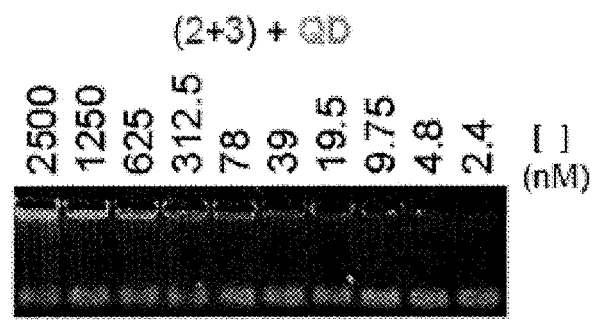

In FIG. 2D it was found that at least a 4:1 ratio of (2+3) duplexes (i.e., coupling species 126) to QDs was needed for lattice formation. In FIG. 2E, the preformed (2+3) duplexes were mixed with QDs, and the complete conversion of free QDs into the lattices was found to take just 30 seconds. It was demonstrated that QD lattices can be easily digested by DNase, releasing free QDs with shorter DNA fragments attached as seen in FIG. 2E. This data confirms that the lattice formation is driven by DNAs. Furthermore, the lowest concentration of lattices required for visualization with the gels was ~5 nM as seen in FIG. 2F.

To test the reassociation of DNA strands in the biosensor and release of duplexes (2+3), a series of assemblies with and without target strands present were analyzed by native-PAGE. The data is presented in FIG. 2G. Reassociation experiments were carried out at different incubation temperatures and the results confirm that the analyte 4 causes the formation of duplexes (1+4) that result in the release of the biotinylated duplexes (2+3) (i.e., coupling species 126).

Figure 2G:
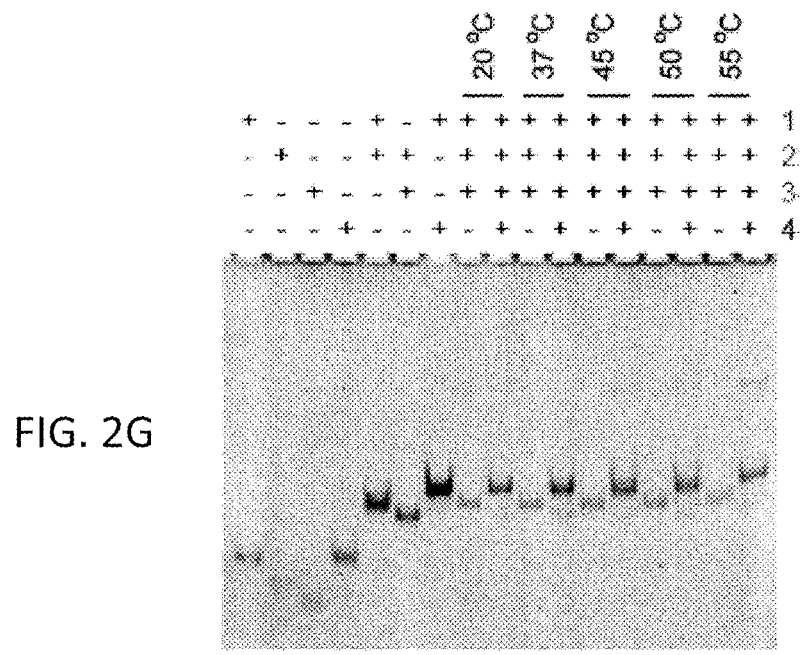
Figure 2H:
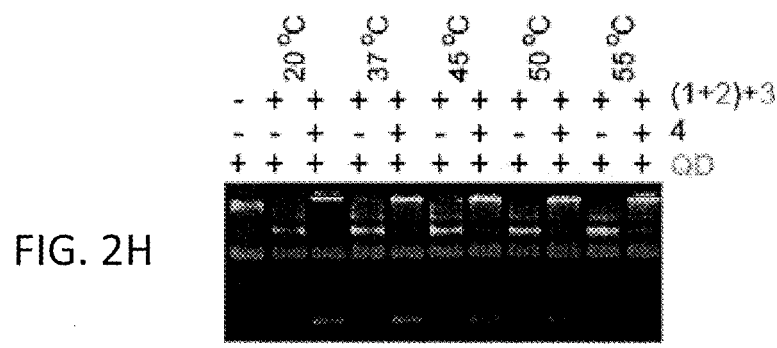
Figures 2I, 2J:
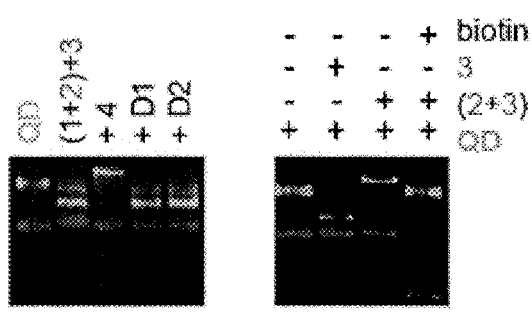

Coupling species 126 were released most efficiently at an incubation temperature of about 37° C. In the same set of experiments, QDs 5 were added to the biosensor composition ((1+2)+3) with and without analyte nucleic acid 4, and analyzed on agarose gels, as shown in FIG. 2H. The cleanest formation of QD lattices occurred at about 20 and 37° C. To test for specificity, two different "dummy" target strands of comparable lengths were tried, and the data is shown in FIG. 2I. Lattice formation was detected only in the presence of the correct target analyte and was completely blocked in the presence of free biotin, as observed in FIG. 2J. The experiments with different amounts of analyte 4 mixed with constant amounts of biosensor composition 124 (i.e., (1+2)+3+QDs) revealed the visible aggregation for ten times excess of sensor to target molecule. Higher order bands were observed in reassociation experiments with the target analyte, especially when elevated incubation temperatures (i.e., 45° C., 50° C., and 55° C.) were used as seen in FIG. 2G. These bands were located higher than expected for double-stranded DNA and point to energetically stable complexes composed of more than two nucleic acids. Simulation results indicate that the analyte 4, guard 1, and anti-guard 2 nucleic acids can form a stable complex which can be maintained at high temperatures (i.e., of about 55-60° C.) and can therefore explain the additional bands observed when the target strand is present.

FIGS. 3A and 3B are representative fluorescence micrographs that show 75 μm square fields containing streptavidin decorated QDs mixed with sensor strands before (3A) and after (3B) the analyte was introduced. The samples were analyzed at ~100 picomolar concentrations, which produced relatively dense particle distributions as seen in FIGS. 3A-3B, which points toward the feasibility of using much lower QD concentrations. Both images are scaled to the same intensity ranges and apart from a few brighter spots in FIG. 3B there is little visual difference between them.

Small regions in FIGS. 3A and 3B were reimaged and shown in FIGS. 3C and 3D, respectively. Diffraction limits the resolution of the fluorescence spots to about 250 nm, so even moderately large QD lattices cannot be distinguished from single QDs by spot size alone; however, the particle in FIG. 3C exhibits streaking in the fluorescence image, which is largely absent from the particle in FIG. 3D. The streaking is due to blinking during a vertical raster scan across the particle and it indicates the presence of a single QD. The absence of streaking in FIG. 3D strongly implies that multiple QDs are located within the focal spot. Note that in the absence of the target strand, the majority (e.g., >90%) of observed particles exhibited single QD blinking dynamics, while just a few were indicative of small groups of co-localized QDs (estimated 2-3 particles). Further evidence of lattice formation is seen in the analysis of the intensity distribution in FIGS. 3A and 3B as shown in FIG. 3E. In the presence of the target analyte strand the intensity histogram (front curve, corresponding to FIG. 3B) has a significantly longer tail than the histogram recorded before the target strand was added (rear curve adjacent y-axis, corresponding to FIG. 3A). The presence of the high intensity spots in FIG. 3B indicates the presence of QD lattices (i.e., aggregated QDs) with many QDs in the detection volume, all of which can contribute to the substantially continuous fluorescence intensity.

Figures 4A, 4B, 4C, 4D:
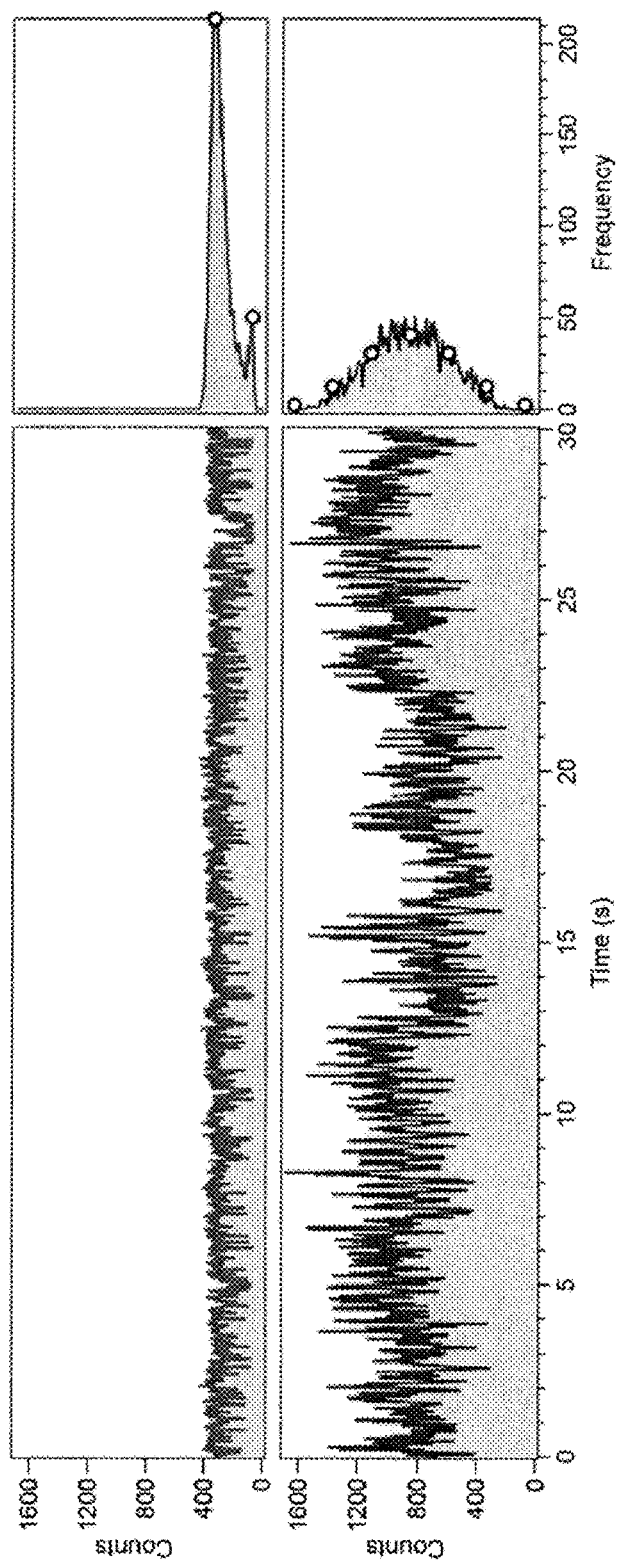
FIGS. 4A and 4B are fluorescence traces recorded on a bright spot from the data of FIGS. 3A and 3B, respectively.
FIGS. 4C and 4D illustrate intensity histogram data for the compositions of FIGS. 4A and 4B, respectively.

The key results that distinguish aggregated QD lattices (formed after introduction of target analyte strands) from individual, non-aggregated QDs are presented in FIG. 4A-4D. Representative fluorescence blinking traces recorded on the bright spot in FIGS. 3A and 3B are shown in FIGS. 4A and 4B, respectively. Each trace has been scaled over the same intensity range. The trace in FIG. 4A fluctuates randomly between bright (~380 counts per 10 ms bin period) and dark (~90 counts/bin) periods and is typical for a single (blinking) QD. An intensity histogram calculated for this trace as seen in FIG. 4C shows two peaks indicating the two intensity distributions (i.e., when blinking on and off).

After introduction of the target analyte strand the trace in FIG. 4B looks considerably different. Instead of binary (bimodal) blinking, the intensity fluctuates over a much wider range, indicative of the QD lattice formation. Although particles in the lattices are still blinking, the total (summed) fluorescence for the whole lattice is rarely completely dark (off) or fully bright (on). This is reflected in the histogram depicted in FIG. 4D, which shows a broad intensity distribution with a mean intensity greater than that in FIG. 4C. Assuming stochastic and independent blinking from each QD in a lattice, a binomial model with single QD bright and dark intensities from FIG. 4C (marked by open circles) were used to predict the expected blinking histograms for QD lattices.

The intensity distribution for six QDs closely matches the measured distribution in FIG. 4D (open circles), suggesting that there are at least six emitting QDs in this particular lattice. This type of analysis is approximate since it relies on the intensity of an unrelated single QD as a basis for the intensity distribution of the QD lattice. Notably, the difference in blinking dynamics and/or characteristics provides a reference-free way to distinguish the presence of QD lattices triggered by the addition of a target analyte strand. A sample that yields bright spots with bimodal trajectories, as in FIG. 4A, clearly contains one or more single (e.g., non-coupled and non-aggregated) QDs, while a sample that yields widely distributed intensity trajectories, as in FIG. 4B, contains aggregated QD lattices and indicates the presence of the target analyte strand. The concentration of QD lattices required for the blinking study is in the picomolar range, which would be hard to detect using an ensemble of fluorescence techniques. Although the analytical performance of biosensor compositions is a complex function of the absolute concentrations of sensor and target analyte strands as well as QD concentration, false positives can be eliminated by surveying a representative number of fluorescent spots.

The systems set forth in this Example comprise biosensor compositions configured to induce or inhibit QD aggregation upon encountering a target molecule or analyte. The observation of quasi-continuous emission indicates its presence. It was observed that DNAs can be programmed to drive rapid isothermal assembly of QDs in the presence of analyte (e.g., oncogene K-ras). The assembled QDs and were readily distinguished from the free QDs by the absence of blinking. The biosensor compositions and methods described herein provide a more robust sensing strategy, which eliminates the need for analyte-induced changes in the fluorescence from individual particles.

Example 2

Compositions and Methods for Sensing

Figure 5:
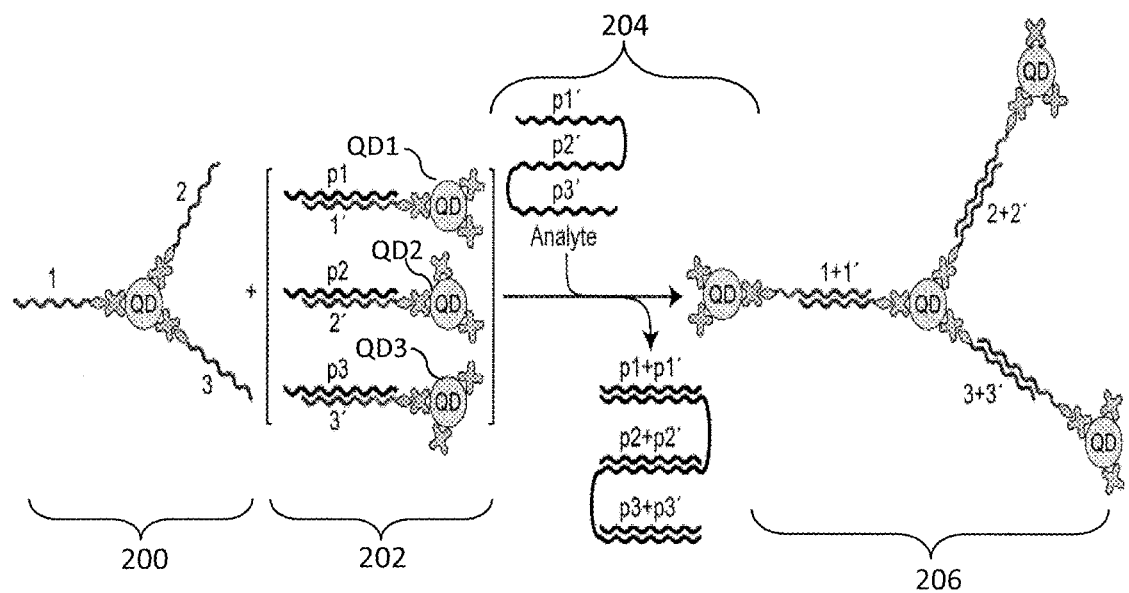
FIG. 5 is a schematic illustration of a biosensing composition and method according to one embodiment described herein.

FIG. 5 schematically illustrates a sensing composition and method that induces and/or causes the aggregation of multiple discrete QDs in the presence of an analyte. In this scheme, the presence of analyte triggers non-blinking fluorescence. As FIG. 5 illustrates, the sensing composition comprises a luminescent species 200, an analyte binding species or composition 202, and a test sample comprising an analyte 204. The luminescent species 200 comprises a colloidal QD having a first single-stranded nucleic acid 1, a second single-stranded nucleic acid 2, and a third single-single stranded nucleic acid 3 attached to an exterior surface thereof.

The analyte binding species 202 comprises a plurality of single-stranded nucleic acids bound to a plurality of complimentary single-stranded nucleic acids and attached to a respective plurality of QDs. For example, the analyte binding species 202 comprises a first single-stranded nucleic acid p1 bound to a first complementary single-stranded nucleic acid 1' and attached to a first quantum dot QD1, a second single-stranded nucleic acid p2 bound to a second complementary single-stranded nucleic acid 2' and attached to a second quantum dot QD2, and a third single-stranded nucleic acid p3 bound to a third complementary single-stranded nucleic acid 3' and attached to a third quantum dot QD3.

The analyte 204 comprises a single-stranded analyte nucleic acid having a first binding moiety p1', a second binding moiety p2', and a third binding moiety p3'. As FIG. 5 illustrates, the first binding moiety p1' is operable to bind to p1, the second binding moiety p2' is operable to bind to p2, and the third binding moiety p3' is operable to bind to p3.

The analyte 204 induces formation of an aggregated QD structure or lattice 206. During reassociation, 1' is operable to bind to 1, 2' is operable to bind to 2, and 3' is operable to bind to 3. The presence of analyte triggers formation of a coupling species via favorable binding conditions. The binding energies of p1' bound to p1, p2' bound to p2, p3' bound to p3, 1' bound to 1, 2' bound to 2, and 3' bound to 3 thermodynamically favor formation of the coupling species.

Example 3

Compositions and Methods for Sensing

Figure 6:
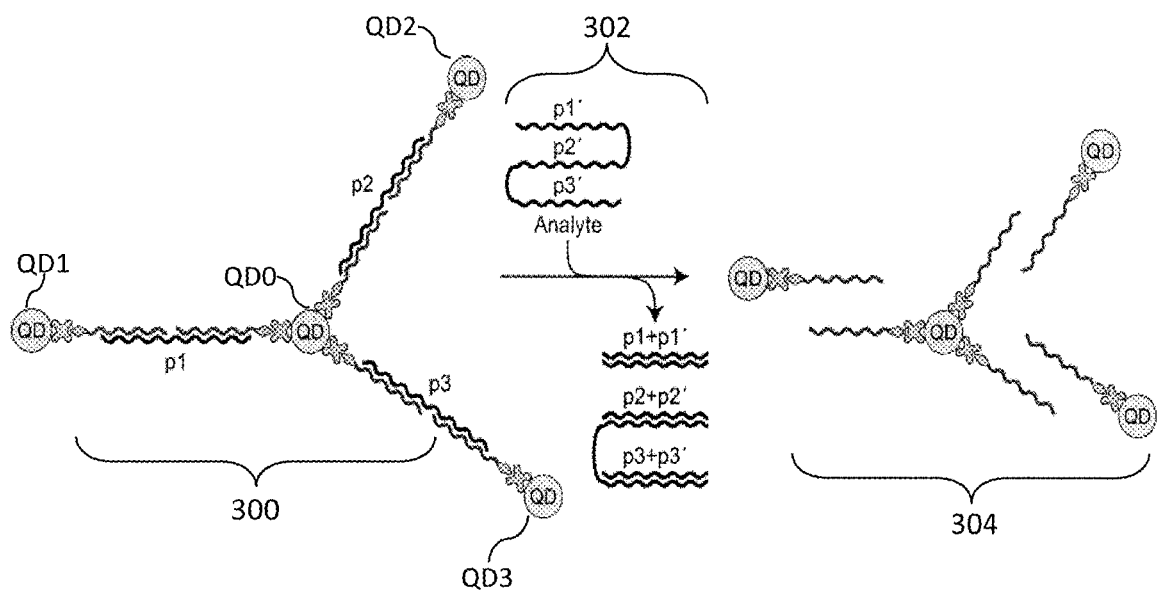
FIG. 6 is a schematic illustration of a biosensing composition and method according to one embodiment described herein.

FIG. 6 schematically illustrates a sensing composition and method that induces and/or causes the de-coupling or disassembly of aggregated QDs in the presence of an analyte. In this scheme, the presence of analyte triggers blinking fluorescence. As FIG. 6 illustrates, a coupled or aggregated luminescent species 300 comprise a colloidal quantum dot (QD0) bound to a first additional quantum dot (QD1), a second additional quantum dot (QD2), and a third additional quantum dot (QD3). The QD0 has a first single-stranded nucleic acid (1), a second single-stranded nucleic acid (2), and a third single-single stranded nucleic acid (3) attached to an exterior surface of the CQD. Additionally, the analyte binding species comprise a first single-stranded nucleic acid (p1) bound to a first complementary single-stranded nucleic acid (1') attached to the QD1 and to (1), a second single-stranded nucleic acid (p2) bound to a second complementary single-stranded nucleic acid (2') attached to the QD2 and to (2), and a third single-stranded nucleic acid (p3) bound to a third complementary single-stranded nucleic acid (3')

attached to the QD3 and to (3). The analyte 302 comprises a single-stranded analyte nucleic acid having a first binding moiety (p1'), a second binding moiety (p2'), and a third binding moiety (p3'). Moreover, binding energies of (p1') bound to (p1), (p2') bound to (p2), (p3') bound to (p3), (1') bound to (1), (2') bound to (2), and (3') bound to (3) thermodynamically favor the decoupling of the QD1, the QD2, and the QD3 from QD0.

Example 4

Compositions and Methods for Sensing

Figure 7:
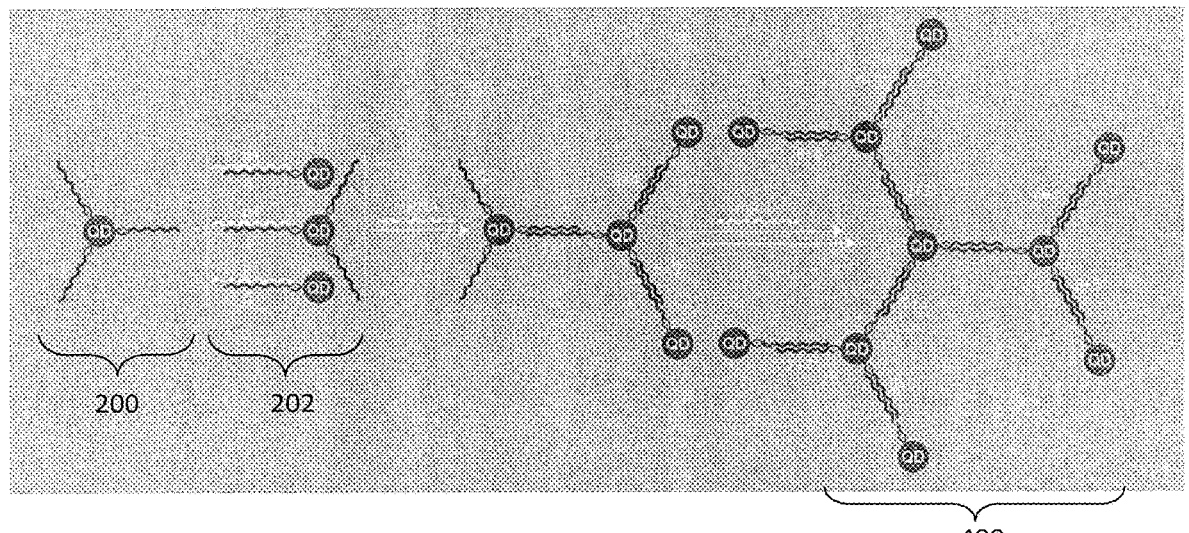
FIG. 7 is a schematic illustration of a biosensing composition and method according to one embodiment described herein.

FIG. 7 schematically illustrates a sensing composition and method that induces formation of a large QD lattice 400 having multiple binding sites in the presence of messenger nucleic acid sequences (mRNA). The biosensor detection limits can be increased via formation of multiple binding sites for one target.

As FIG. 7 illustrates, the biosensor comprises a luminescent species 200 and an analyte binding species or composition 202 that triggers formation of the QD lattice 400 via cross-linking the luminescent species of 200 and 202 in the presence of one or more mRNA sequences. The luminescent species 200 is described in Example 2 above. However, the analyte binding species 202 comprises additional coupling moieties that can be used to facilitate a "cascading" aggregation of QDs, which is triggered by the presence of the mRNA.

Example 5

Compositions and Methods for Sensing

Figure 8:
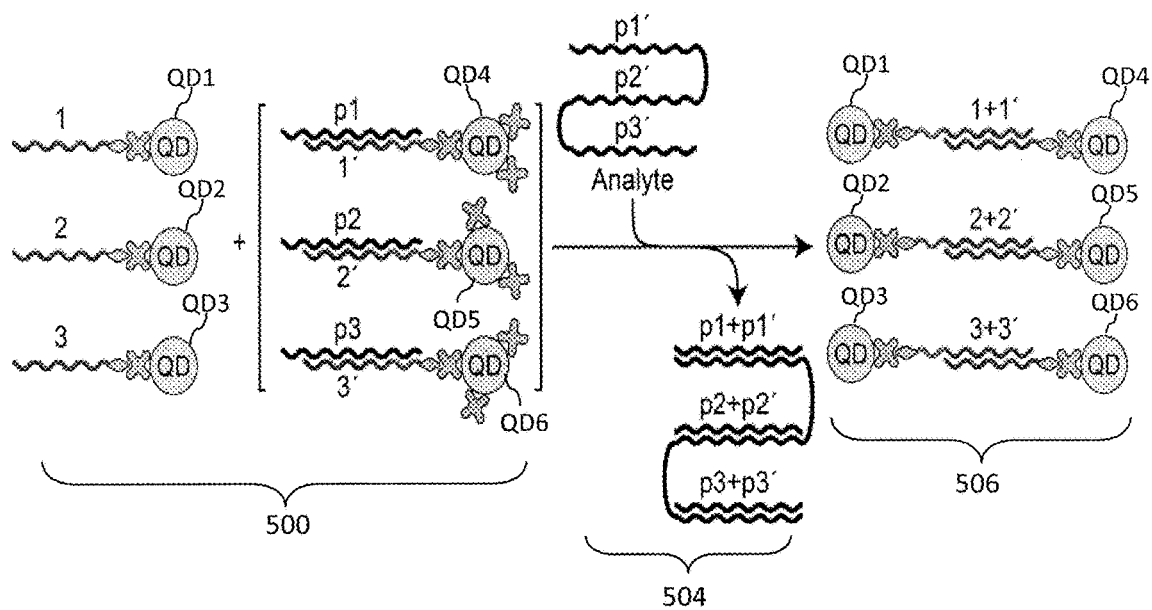
FIG. 8 is a schematic illustration of a biosensing composition and method according to one embodiment described herein.

FIG. 8 schematically illustrates a sensing composition and method that induces formation of smaller QD aggregates in the presence of an analyte. In this embodiment, the presence of analyte triggers the observation of non-blinking fluorescence.

As FIG. 8 illustrates, the biosensor comprises a biosensing composition 500 comprising a luminescent species and a test sample comprising an analyte 504. The luminescent species comprises a plurality of QDs bound to a plurality of binding moieties. For example, a first QD1 is bound to a first binding moiety 1, a second QD2 is bound to a second binding moiety 2, and a third QD3 is bound to a third binding moiety 3.

The biosensor composition 500 further comprises a plurality of QDs bound to a plurality of analyte binding species. For example, the composition 500 further comprises a first single-stranded nucleic acid p1 bound to a first complementary single-stranded nucleic acid 1' and attached to a fourth QD4, a second single-stranded nucleic acid p2 bound to a second complementary single-stranded nucleic acid 2' and attached to a fifth QD5, and a third single-stranded nucleic acid p3 bound to a third complementary single-stranded nucleic acid 3' and attached to a sixth QD6.

The presence of analyte 504 triggers formation of a plurality of smaller aggregates 506. The analyte comprises a first single-stranded nucleic acid p1', a second single-stranded nucleic acid p2', and a third single-stranded nucleic acid p3'. Smaller aggregates 406 form upon binding the analyte binding species (i.e., p1-p3) to the respective single-stranded nucleic acids (i.e., p1'-p3') of the analyte and the binding of first binding moiety 1 to 1', the second binding moiety 2 to 2', and the third binding moiety 3 to 3' in the presence of analyte 504. The binding energies of 1' bound to 1, 2' bound to 2, and 3' bound to 3 thermodynamically favors the formation of smaller QD aggregates.

Detection limits may be improved via formation of smaller aggregates from a single analyte interaction. For example, the scheme in FIG. 8 illustrates a method of generating multiple QD assemblies after interaction with a single analyte molecule. This scheme could also be done in reverse for decoupling the smaller aggregates for lowering the detection limit of the sensor.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of sensing comprising:
disposing an analyte binding species in a test sample;
disposing a population of luminescent species in the test sample after disposing the analyte binding species in the test sample;
exposing the test sample to electromagnetic radiation having a wavelength corresponding to an excitation wavelength of the luminescent species;
detecting light emitted by the luminescent species within a detection region of the test sample; and
correlating the light emitted by the luminescent species within the detection region to a presence or absence of an analyte within the test sample in an amount above a minimum detection threshold,
wherein the luminescent species, in a non-aggregated state, exhibits luminescence blinking, and, in an aggregated state, does not exhibit luminescence blinking;
wherein correlating the light emitted by the luminescent species within the detection region to the presence or absence of the analyte within the test sample comprises determining whether the light emitted by the luminescent species within the detection region is blinking luminescence or non-blinking luminescence;
wherein the population of luminescent species, when initially disposed in the test sample, is in the non-aggregated state; and the presence of the analyte within the test sample causes the population of luminescent species to transition from the non-aggregated state to the aggregated state, resulting in detection of non-blinking luminescence;
wherein the analyte binding species, in the presence of the analyte, binds to the analyte and forms a coupling species;
wherein the analyte binding species, in the absence of the analyte, does not form the coupling species;
wherein the coupling species formed in the presence of the analyte is operable to couple a plurality of the luminescent species to one another; and wherein:
the luminescent species, in the non-aggregated state, comprises colloidal quantum dots having one or more first coupling moieties attached to exterior surfaces of the colloidal quantum dots;
the analyte comprises a single-stranded analyte nucleic acid;
the analyte binding species comprises a double-stranded nucleic acid consisting of a single-stranded guard nucleic acid bound to a single-stranded anti-guard nucleic acid;
the anti-guard nucleic acid has a terminus comprising a toehold nucleic acid segment and comprising a second coupling moiety that is operable to selectively bind to the one or more first coupling moieties of the colloidal quantum dots;

the guard nucleic acid is operable to bind to the analyte nucleic acid;

the anti-guard nucleic acid is operable to bind to a single-stranded complementary anti-guard nucleic acid;

the complementary anti-guard nucleic acid has a terminus comprising a third coupling moiety that is operable to selectively bind to the one or more first coupling moieties of the colloidal quantum dots;

the coupling species comprises a double-stranded nucleic acid consisting of the anti-guard nucleic acid bound to the complementary anti-guard nucleic acid such that the second coupling moiety and the third coupling moiety are on opposite terminuses of the coupling species; and binding energies of (a) the analyte nucleic acid to the guard nucleic acid, (b) the guard nucleic acid to the anti-guard nucleic acid, and (c) the anti-guard nucleic acid to the complementary anti-guard nucleic acid thermodynamically favor formation of the coupling species.

2. The method of claim 1, wherein:
the one more first coupling moieties comprise streptavidin; and
second coupling moiety and the third coupling moiety comprise biotin or avidin.

3. A method of sensing comprising:
disposing an analyte binding species in a test sample;
disposing a population of luminescent species in the test sample after disposing the analyte binding species in the test sample;
exposing the test sample to electromagnetic radiation having a wavelength corresponding to an excitation wavelength of the luminescent species;
detecting light emitted by the luminescent species within a detection region of the test sample; and
correlating the light emitted by the luminescent species within the detection region to a presence or absence of an analyte within the test sample in an amount above a minimum detection threshold,
wherein the luminescent species, in a non-aggregated state, exhibits luminescence blinking, and, in an aggregated state, does not exhibit luminescence blinking;
wherein correlating the light emitted by the luminescent species within the detection region to the presence or absence of the analyte within the test sample comprises determining whether the light emitted by the luminescent species within the detection region is blinking luminescence or non-blinking luminescence;
wherein the population of luminescent species, when initially disposed in the test sample, is in the non-aggregated state; and the presence of the analyte within the test sample causes the population of luminescent species to transition from the non-aggregated state to the aggregated state, resulting in detection of non-blinking luminescence;
wherein the analyte binding species, in the presence of the analyte, binds to the analyte and forms a coupling species;
wherein the analyte binding species, in the absence of the analyte, does not form the coupling species;
wherein the coupling species formed in the presence of the analyte is operable to couple a plurality of the luminescent species to one another; and wherein:

the luminescent species, in the non-aggregated state, comprises a colloidal quantum dot (CQD) having a first single-stranded nucleic acid (1), a second single stranded nucleic acid (2), and a third single-single stranded nucleic acid (3) attached to an exterior surface of the CQD;

the analyte comprises a single-stranded analyte nucleic acid having a first binding moiety (p1'), a second binding moiety (p2'), and a third binding moiety (p3');

the analyte binding species comprises a first single stranded nucleic acid (p1) bound to a first complementary single-stranded nucleic acid (1') attached to a first quantum dot (QD1), a second single-stranded nucleic acid (p2) bound to a second complementary single stranded nucleic acid (2') attached to a second quantum dot (QD2), and a third single-stranded nucleic acid (p3) bound to a third complementary single-stranded nucleic acid (3') attached to a third quantum dot (QD3);

(p1') is operable to bind to (p1);
(p2') is operable to bind to (p2);
(p3') is operable to bind to (p3);
(1') is operable to bind to (1);
(2') is operable to bind to (2);
(3') is operable to bind to (3);
the coupling species comprises a species in which (1') is bound to (1), (2') is bound to (2), and (3') is bound to (3); and
binding energies of (p1') bound to (p1), (p2') bound to (p2), (p3') bound to (p3), (1') bound to (1), (2') bound to (2), and (3') bound to (3) thermodynamically favor formation of the coupling species.

4. A method of sensing comprising:
disposing a population of luminescent species in a test sample;
exposing the test sample to electromagnetic radiation having a wavelength corresponding to an excitation wavelength of the luminescent species;
detecting light emitted by the luminescent species within a detection region of the test sample; and
correlating the light emitted by the luminescent species within the detection region to a presence or absence of an analyte within the test sample in an amount above a minimum detection threshold,
wherein the luminescent species, in a non-aggregated state, exhibits luminescence blinking and, in an aggregated state, does not exhibit luminescence blinking;
wherein correlating the light emitted by the luminescent species within the detection region to the presence or absence of the analyte within the test sample comprises determining whether the light emitted by the luminescent species within the detection region is blinking luminescence or non-blinking luminescence;
wherein the population of luminescent species, when initially disposed in the test sample, is in the aggregated state; and the presence of the analyte within the test sample causes the population of luminescent species to transition from the aggregated state to the non-aggregated state, resulting in detection of blinking luminescence;
wherein individual luminescent species in the population of luminescent species in the aggregated state are coupled to one another by one or more analyte binding species;
wherein the one or more analyte binding species, in the presence of the analyte, preferentially binds to the analyte and unbinds from the coupled individual luminescent species, thereby decoupling the individual luminescent species from one another;

wherein the one or more analyte binding species, in the absence of the analyte, does not substantially unbind from or decouple the coupled individual luminescent species from one another; and wherein:

the coupled individual luminescent species comprises a colloidal quantum dot (CQD) bound to a first additional quantum dot (QD1), a second additional quantum dot (QD2), and a third additional quantum dot (QD3);

the CQD has a first single-stranded nucleic acid (1), a second single-stranded nucleic acid (2), and a third single-single stranded nucleic acid (3) attached to an exterior surface of the CQD;

the analyte binding species comprise a first single stranded nucleic acid (p1) bound to a first complementary single-stranded nucleic acid (1') attached to the QD1 and to (1), a second single-stranded nucleic acid (p2) bound to a second complementary single-stranded nucleic acid (2') attached to the QD2 and to (2), and a third single-stranded nucleic acid (p3) bound to a third complementary single-stranded nucleic acid (3') attached to the QD3 and to (3);

the analyte comprises a single-stranded analyte nucleic acid having a first binding moiety (p1'), a second binding moiety (p2'), and a third binding moiety (p3'); and binding energies of (p1') bound to (p1), (p2') bound to (p2), (p3') bound to (p3), (1') bound to (1), (2') bound to (2), and (3') bound to (3) thermodynamically favor the decoupling of the QD1, the QD2, and the QD3 from the CQD.

5. The method of claim 4, wherein:

the one or more analyte binding species couples the individual luminescent species to one another via one or more coupling moieties of the individual luminescent species.

* * * * *